(12) United States Patent
Stephenson et al.

(10) Patent No.: US 7,231,305 B2
(45) Date of Patent: Jun. 12, 2007

(54) FLOW RATE DETERMINATION

(75) Inventors: Kenneth Edward Stephenson, Newtown, CT (US); Lalitha Venkataramanan, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/911,871

(22) Filed: Aug. 5, 2004

(65) Prior Publication Data

US 2005/0033530 A1   Feb. 10, 2005

Related U.S. Application Data

(60) Provisional application No. 60/493,134, filed on Aug. 7, 2003.

(51) Int. Cl.
*G01F 1/00* (2006.01)
(52) U.S. Cl. .......................... 702/45; 702/50
(58) Field of Classification Search ............ 702/23, 702/45, 50–51, 138
See application file for complete search history.

(56) References Cited

U.S. PATENT DOCUMENTS

| | | | |
|---|---|---|---|
| 5,637,791 A * | 6/1997 | Alonso | 73/64.45 |
| 6,604,054 B2 * | 8/2003 | Lipscomb et al. | 702/47 |
| 6,681,189 B1 * | 1/2004 | Morrison et al. | 702/45 |
| 6,859,740 B2 * | 2/2005 | Stephenson et al. | 702/35 |
| 6,907,383 B2 * | 6/2005 | Eryurek et al. | 702/183 |
| 2002/0173923 A1 * | 11/2002 | Schutzbach et al. | 702/45 |
| 2004/0260484 A1 * | 12/2004 | Wray | 702/45 |
| 2004/0260497 A1 * | 12/2004 | DiFoggio et al. | 702/98 |

OTHER PUBLICATIONS

Golan, M. and Whitson, C.H. *Well Performance Second Edition*. Prentice Hall, Inc. (1991) pp. 29-46.
Madisetti, v. k. and Williams, D.B. *The Digital Signal Processing Handbook*. IEEE Press (1998) Chapter 21 Recursive Least-Squares Adaptive Filters, pp. 21-1-21-37.
Press, W. H. et al. *Numerical Recipes in C, The Art of Scientific Computing Second Edition*. Cambridge University Press (1998) pp. 190-194.

* cited by examiner

*Primary Examiner*—John Barlow
*Assistant Examiner*—Jonathan Moffat
(74) *Attorney, Agent, or Firm*—Steven McHugh; Jody Lynn DeStefanis; Dale Gaudier

(57) ABSTRACT

A method for determining the bubble point pressure and the true flow rate of a fluid in a flow line of a flowing well is provided, wherein the method includes modifying fluid pressure in a predetermined region of the flow line, generating pressure data responsive to the flow line, obtaining apparent flow rate data responsive to the pressure data, examining the apparent flow rate data to identify a discontinuity in the apparent flow rate data and generating true flow rate data responsive to the discontinuity.

25 Claims, 19 Drawing Sheets

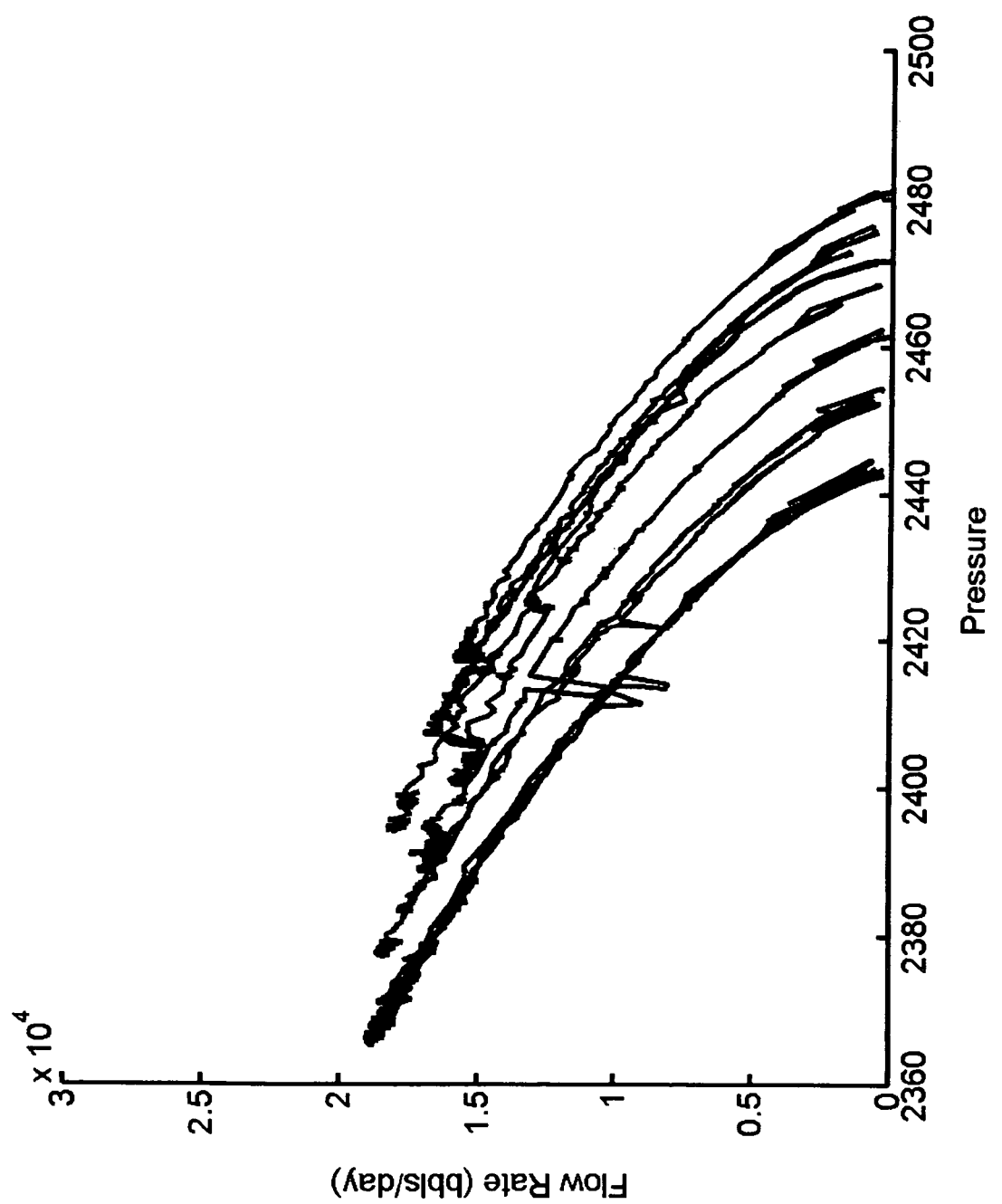

FLOW RATE DETERMINATION

RELATED APPLICATIONS

This Application claims priority of U.S. Provisional Patent Application No. 60/493,134 filed Aug. 7, 2003 the contents of which are hereby incorporated by reference herein in its entirety.

FIELD OF THE INVENTION

The present invention relates generally to the flow of a fluid within a flow-line and more particularly to the determination of the flow rate of a fluid flowing within a flow-line.

BACKGROUND OF THE INVENTION

The determination of the flow rate of fluids flowing within a well is important to the monitoring and control of the movement of the fluids in the well and reservoir. For example, by monitoring the flow rates of both oil and water from each zone of a well, the water production of the entire well may be controlled by reducing the flow from those zones that produce the highest water cut (i.e., ratio of water flow rate to total flow rate), allowing the reservoir oil to be swept more completely during the life of the well.

One common method for determining the velocity of a fluid in a flow stream involves disposing a turbine blade within the flow stream and measuring the rotational velocity of the turbine blade. In single phase flow conditions, the rotational velocity of the turbine blade is simply related to the velocity of the flow stream. Unfortunately however, in multiple phase flow conditions, such as in a mixed oil and water flow condition, the response of the turbine can be so complicated that the results may not be interpretable. Another method for determining the velocity of a fluid in a flow stream involves injecting a tracer substance into the fluid phase of choice (oil or water) and measuring the time it takes for the tracer substance to travel a known distance in the flow stream. The velocity may then be computed using the known distance and the time of travel. One disadvantage of this method for permanent down-hole use is the need for a reservoir of tracer material and a mechanical tracer injector. Because the reservoir and injector are permanently disposed down-hole in the well, the number of velocity measurements is limited by the quantity of tracer material and the injector is prone to sticking and failure.

Another method for determining the velocity of a fluid in a flow stream involves using local capacitance or resistance sensors. However, this method is only appropriate for flow regimes in which one phase is dispersed as droplets in another continuous phase. As a droplet passes one of the sensors, a signal is produced for a time duration related to the speed of the droplet. Given knowledge of the droplet size by other means, the velocity of the droplet, and hence the fluid flow, can be deduced. One disadvantage of this method is that it does not work at all in a stratified flow regime because it relies on the existence of bubbles.

Another method for determining the flow rate of a fluid in a flow stream involves using a Venturi to measure the total volumetric flow rate. Unfortunately however, due to insensitivity to errors in density and/or pressure determinations, this method may be inaccurate and thus, unreliable.

As such it is an objective of the invention to provide a method for determining the true flow rate of a fluid flowing in a flow line of a well. It is another objective of the invention to provide a method for identifying the bubble point of a fluid flowing in a flow line of a well.

SUMMARY OF THE INVENTION

A method for determining the true flow rate of a fluid in a flow line of a flowing well is provided, wherein the method includes modifying fluid pressure in a predetermined region of the flow line, generating pressure data responsive to the flow line, obtaining apparent flow rate data responsive to the pressure data, examining the apparent flow rate data to identify a discontinuity in the apparent flow rate data and generating true flow rate data responsive to the discontinuity.

A method for determining the bubble point of a fluid in a flow line of a flowing well is provided, wherein the method includes modifying the pressure of the fluid in a predetermined region of the flow line and generating pressure data responsive to the flow line. The pressure data is examined to identify a discontinuity in the pressure data and the absolute pressure is recorded in a manner responsive to the discontinuity. The absolute pressure is then identified as the bubble point pressure.

A method for identifying an occurrence of cavitation in a fluid flowing in a flow line is provided, wherein the method includes generating true flow rate data responsive to the fluid via a method for determining a true flow rate including modifying a characteristic of the fluid, generating fluid data responsive to the characteristic, acquiring apparent flow rate data responsive to the fluid data, examining the apparent flow rate data to identify a discontinuity and generating the true flow rate data responsive to the discontinuity, generating fluid density data responsive to the fluid flowing, communicating the true flow rate data and the fluid density data to a processing device and processing at least one of the true flow rate data and the fluid density data to determine whether cavitation has occurred.

A machine-readable computer program code, the program code including instructions for causing a controller to implement a method for determining the true flow rate of a fluid in a flow line of a flowing well is provided, wherein the method includes modifying fluid pressure in a predetermined region of the flow line, generating pressure data responsive to the flow line, obtaining apparent flow rate data responsive to the pressure data, examining the apparent flow rate data to identify a discontinuity in the apparent flow rate data and analyzing the discontinuity to generate true flow rate data.

BRIEF DESCRIPTION OF THE FIGURES

The foregoing and other features and advantages of the present invention will be more fully understood from the following detailed description of illustrative embodiments, taken in conjunction with the accompanying drawings in which like elements are numbered alike in the several Figures:

FIG. 15(b) is a graph showing the fluid pressure relationship of the true flow rate over a period of eight (8) months.

DETAILED DESCRIPTION OF THE INVENTION

Figure 1:
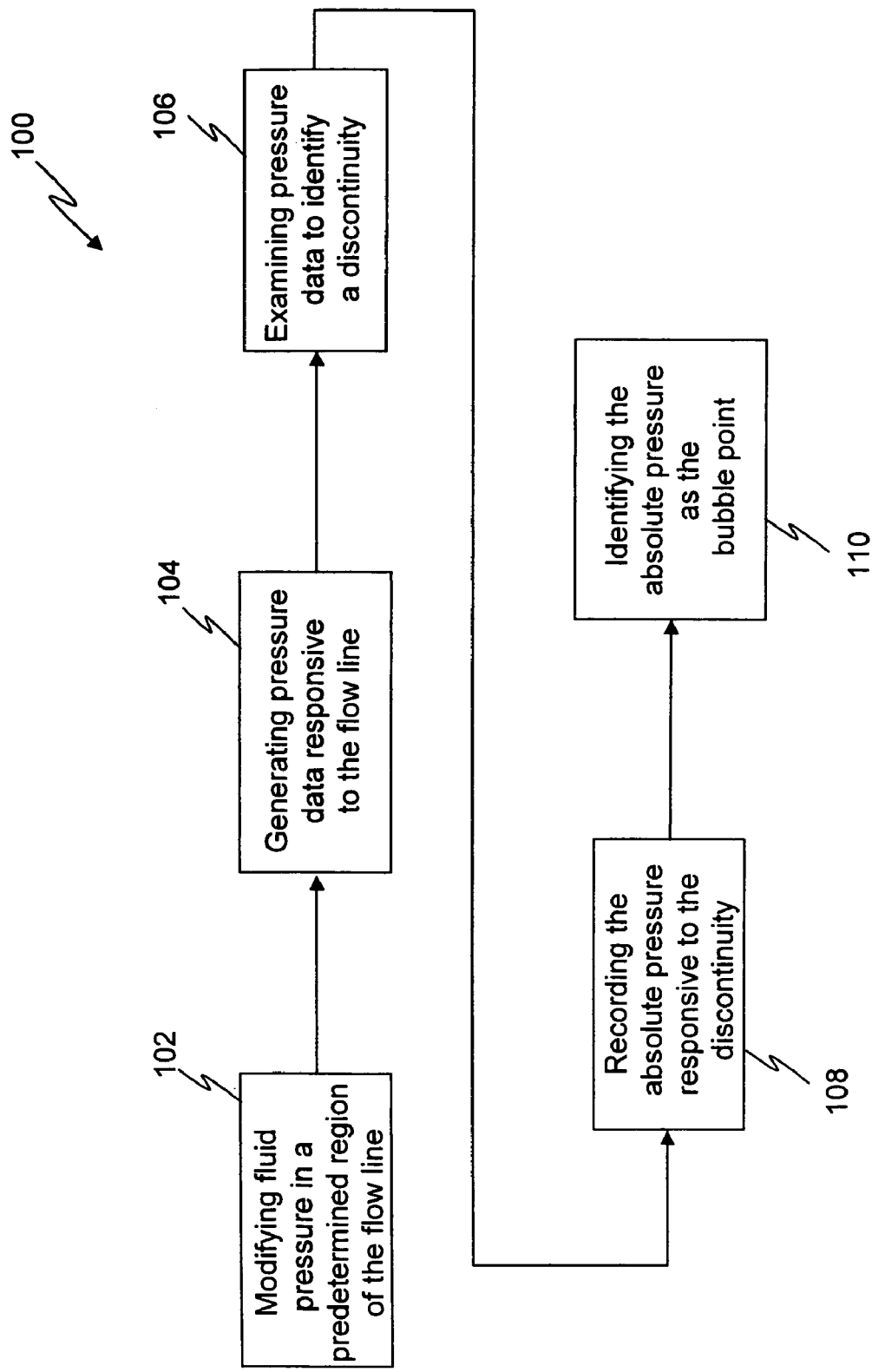
FIG. 1 is a block diagram illustrating a method for determining the bubble point of a fluid flowing in a flow line.

It should be appreciated that for engineers and scientists that are tasked with optimizing the extraction of a hydrocarbon fluid(s) flowing in a flow line from a well, some characteristic properties of these fluids are of great interest. For example, it is highly desirable to be able to determine the bubble point pressure of a fluid flowing in a well, wherein the bubble point pressure is that fluid pressure when gas first begins to evolve from the fluid. This is because, if the reservoir pressure drops below the bubble point pressure during production, a gas bubble will form in the porous reservoir rock and the relative permeability to the oil phase will decrease dramatically. The bubble point of such a fluid may be ascertained by identifying when cavitation, i.e. when gas has come out of solution, has occurred in the fluid. Conveniently enough, the occurrence of cavitation may manifest itself as a discontinuity, or dp_jump, in the flow rate.

Thus, the bubble point of a fluid flowing in a flow line may be determined by identifying the pressure at which cavitation has occurred. One method 100 for determining the bubble point of a fluid in a flow line of a flowing well is provided in FIG. 1, wherein the method 100 includes modifying the pressure of the fluid in a predetermined region of the flow line, as shown in block 102, and generating pressure data responsive to the flow line, as shown in block 104. The pressure data is examined to identify a discontinuity in the pressure data, as shown in block 106, and the absolute pressure is recorded in a manner responsive to the discontinuity, as shown in block 108. The absolute pressure is then identified as the bubble point pressure, as shown in block 110.

Unfortunately, this task is complicated by the fact that current methods to determine flow rate are inaccurate and thus, only identify an apparent flow rate and as such, the true flow rate is unknown. The apparent flow rate is a flow rate which is not adjusted for discontinuities in the pressure data, such as dp_jump. However, as discussed hereinabove, in order to optimize the fluid extraction, it is desirable to keep the pressure in the reservoir above the bubble-point pressure, a task made easier once the bubble point pressure is known. In order to accomplish this task in a cost effective manner, the true flow rate of a fluid flowing in a flow line of a well needs to be determined in a reliable, consistent and accurate manner.

Figure 2:
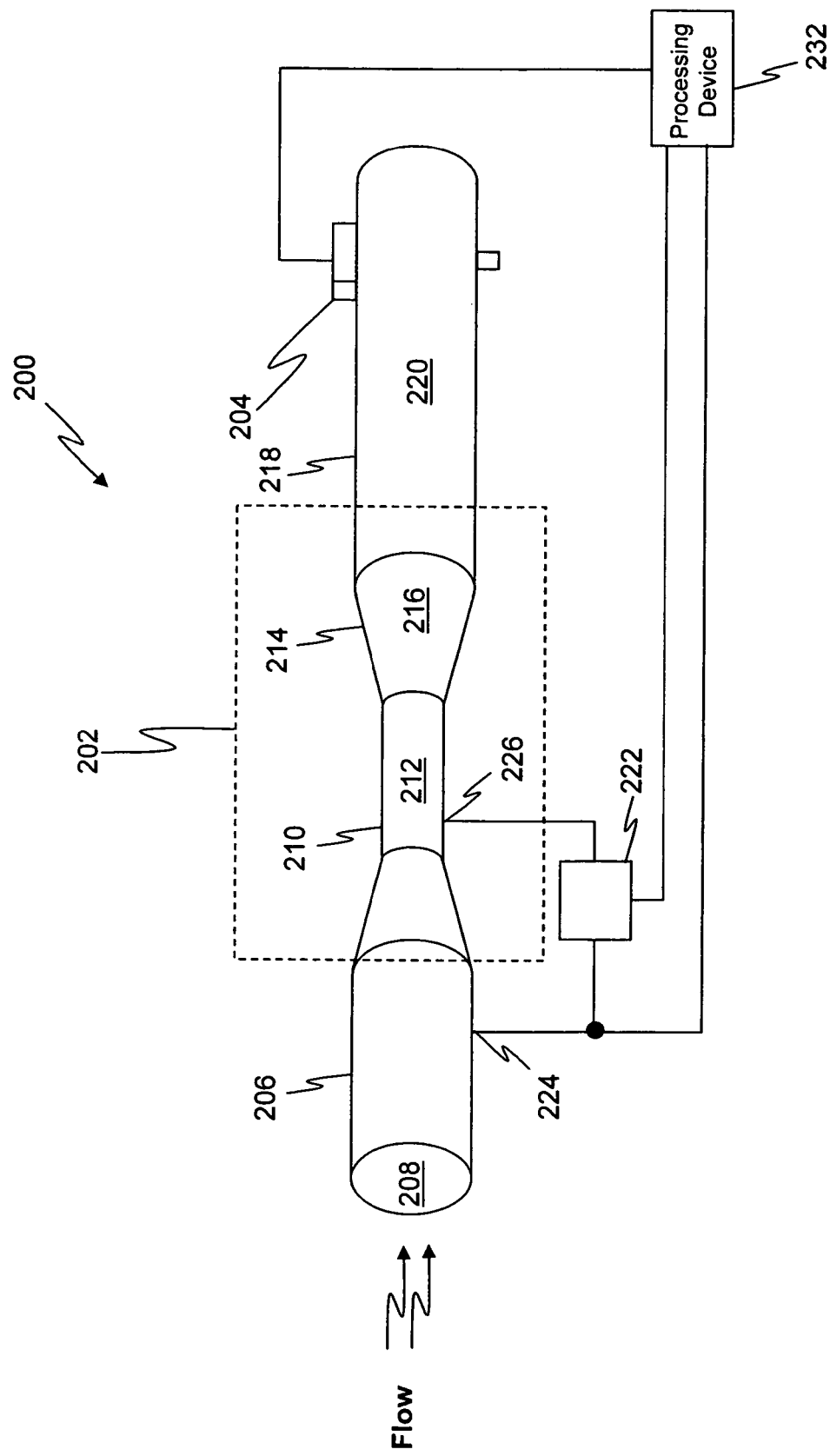
FIG. 2 is a side view of a flow meter, in accordance with an exemplary embodiment.

Referring to FIG. 2, a device for determining the true flow rate of a fluid flowing in a flow line of a well is shown and includes a flow meter 200 which uses a Venturi 202 in combination with a fluid density measuring device 204. Venturi 202 includes a Venturi inlet portion 206 defining an inlet cavity 208, a Venturi throat portion 210 defining a throat cavity 212, a Venturi diffuser portion 214 defining a diffuser cavity 216 and a Venturi pipe portion 218 defining a pipe cavity 220, wherein Venturi inlet portion 206 is communicated with Venturi throat portion 210 which is further communicated with Venturi pipe portion 218 via Venturi diffuser portion 214, such that inlet cavity 208 is communicated with throat cavity 212 which is further communicated with pipe cavity 220 via diffuser cavity 216. Venturi 202 also includes a pressure sensor 222 having a first pressure sensor lead 224 and a second pressure sensor lead 226, wherein first pressure sensor lead 224 is disposed to measure the pressure within Venturi inlet portion 206 and wherein second pressure sensor lead 226 is disposed to measure the pressure within Venturi throat portion 210. It should be appreciated that pressure sensor 222 allows for the measurement of the pressure differential between Venturi inlet portion 206 and Venturi throat portion 210.

A processing device 232 is also provided and is associated with fluid density measuring device 204, first pressure sensor lead 224 and differential pressure sensor 222. It should be appreciated that pressure sensor 222 and/or fluid density measuring device 204 may be any pressure measuring device and/or density measuring device, respectively, suitable to the desired end purpose. It should also be appreciated that processing device 232 may be communicated with pressure sensor 222 and/or fluid density measuring device 204, in whole or in part, via any method suitable to the desired end purpose, such as hard wire communication, wireless communication or any combination thereof.

Figure 3:
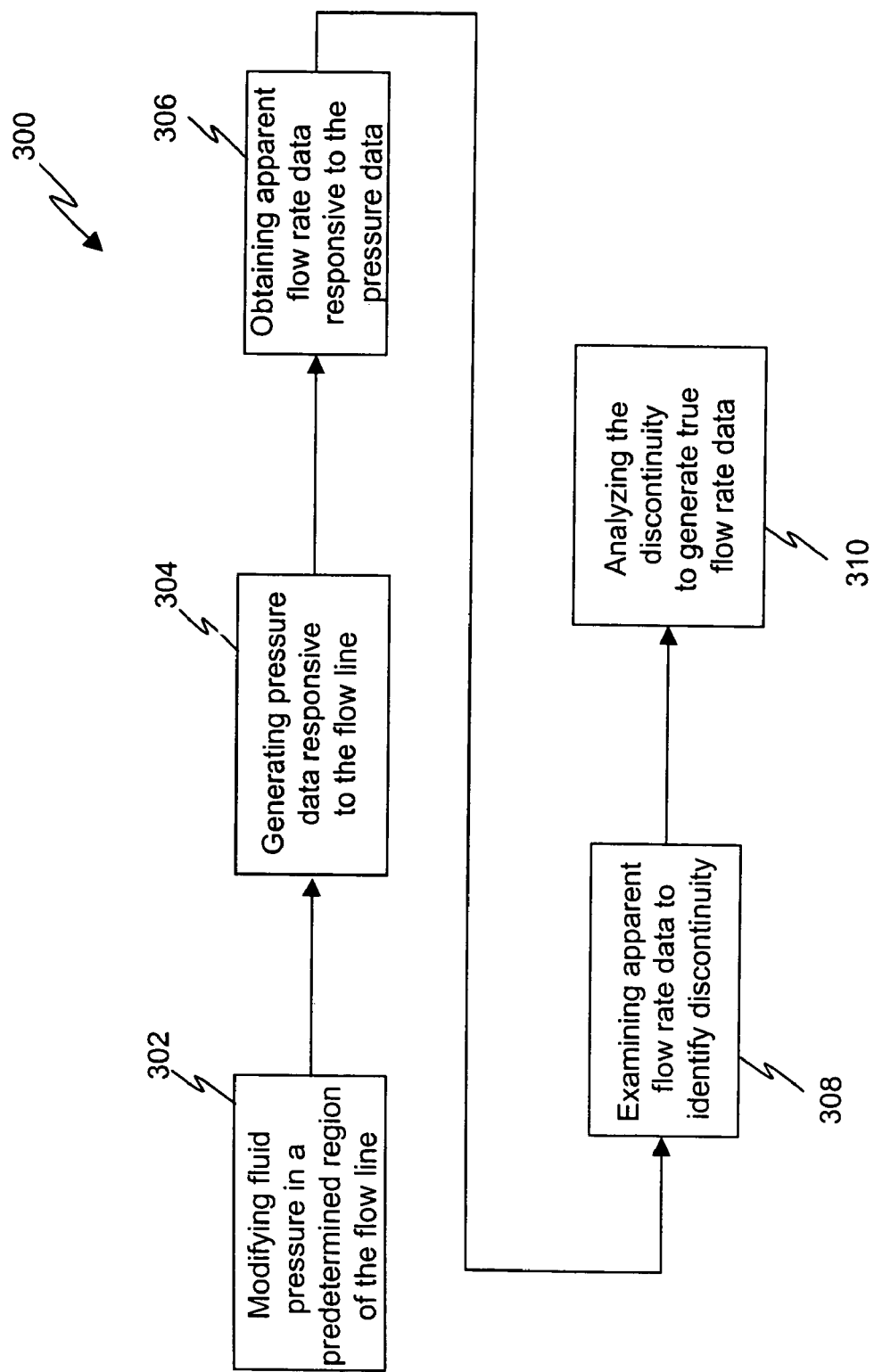
FIG. 3 is a block diagram illustrating a method for determining the true flow rate of a fluid flowing in a flow line.

Referring to FIG. 3, a high level block diagram illustrating a method 300 for determining the true flow rate of a fluid flowing in a flow line of a well is shown and includes modifying the pressure of a fluid flowing through a well pipe in a predetermined region of the flow line in the well pipe, as shown in block 302. Pressure data responsive to the flow line is generated, as shown in block 304, and the pressure data is then used to obtain apparent flow rate data, as shown in block 306. The apparent flow rate data is then examined to determine if a dp_jump has occurred in the apparent flow rate data, as shown in block 308, wherein a dp_jump is defined as a discontinuity in the apparent flow data. The discontinuity is then analyzed to generate true flow rate data, as shown in block 310. It should be appreciated that flow rate data does not necessarily have to be measured in order to determine whether a discontinuity has occurred. There are many other methods to determine that a discontinuity has occurred, such as examining the relationship between fluid density and fluid pressure.

Figure 4:
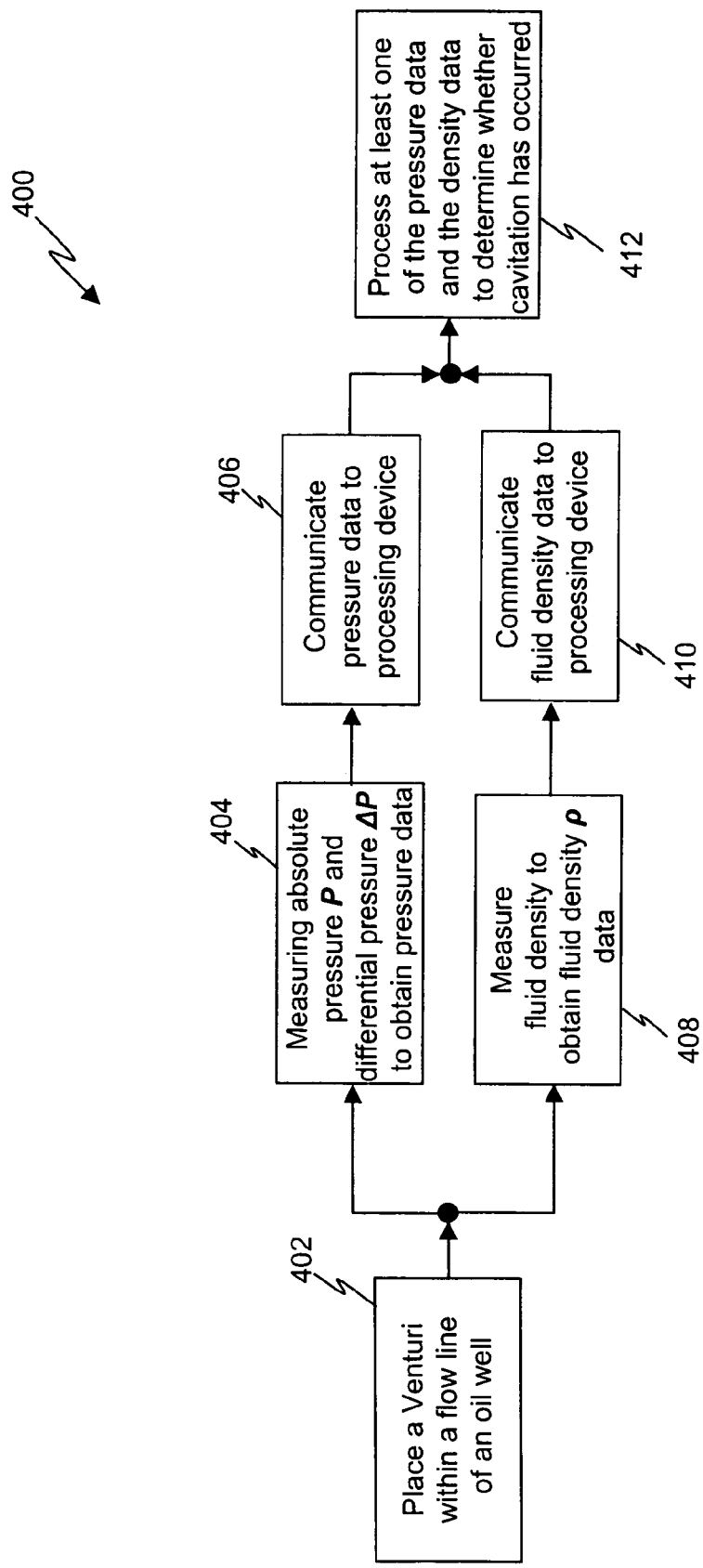
FIG. 4 is a block diagram illustrating a method for identifying an occurrence of cavitation in fluid flowing in a flow meter.

It should be appreciated that method 300 allows for the accurate and reliable determination of the true flow rate of a fluid flowing in a flow line and as such, allows for the occurrence of cavitation to be accurately and correctly identified. Referring to FIG. 4, a block diagram illustrating a method 400 for identifying an occurrence of cavitation in a flow meter is shown and described in terms of a fluid flowing through a Venturi and includes obtaining a Venturi disposed within an oil well, as shown in block 402. The absolute pressure P and the differential pressure ΔP between the Venturi inlet portion 206 and Venturi throat portion 210 is monitored to generate pressure data, as shown in block 404, wherein the pressure data is communicated to a processing device 232, as shown in block 406. Additionally, the density of the fluid may be optionally monitored to generate fluid density data, as shown in block 408, wherein the generated fluid density data may also be communicated to a processing device 232, as shown in block 410. The processing device 232 processes at least one of the pressure data and the fluid density data to determine whether cavitation has occurred, as shown in block 412.

Figure 5:
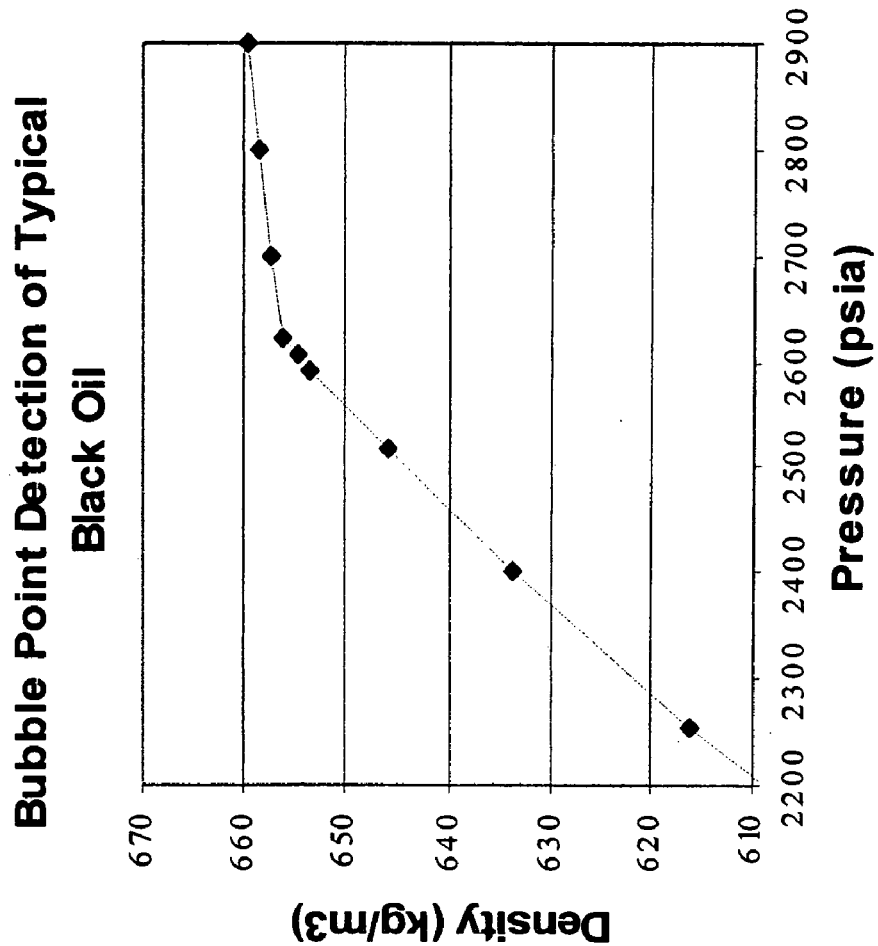
FIG. 5 is a graph of Density versus Pressure for a typical black oil, in accordance with the prior art.

In accordance with an exemplary embodiment, the occurrence of cavitation may be determined using known relationships between pressure and fluid density, wherein the relationship is as illustrated in the following example: Consider the case of a "black oil" hydrocarbon fluid, the density of which varies with pressure. In this case, measuring the density of the fluid as a function of pressure is a common technique that may be used to determine the bubble point. Referring to FIG. 5, the dependency of density on pressure of the black oil is shown and indicates an approximately linear relationship above and below the bubble point, which is located near 2600 psia (i.e. where the slope of density vs. pressure abruptly changes). As can be seen, the compressibility of the fluid (i.e. change in density vs. pressure) is significantly less above the bubble point than it is below the bubble point. This can be verified by the following analysis. Assume, for purposes of illustration, that above the bubble point the density is constant with pressure and that below the bubble point the density varies linearly with pressure. Given this, the density ρ may be represented as a function of absolute pressure P:

$$\rho = aP + b, \tag{1}$$

where a and b are the slope and offset, respectively. If additional assumptions were made as to there being a frictionless and inviscid (not incompressible) flow, as well as that the kinetic energy/unit mass and pressure energy/unit mass were conserved in the flow, then neglecting any thermal transfers from expansion or Joule-Thomson effects, equation (1) can be represented as:

$$\frac{u^2}{2} + \frac{P}{\rho} = M, \tag{2}$$

where u is velocity and M is a constant. Thus, it can be seen that as fluid moves through a Venturi, the kinetic energy and pressure energy will have to change in order to maintain a constant energy. As such, the pressure energy changes will include both pressure changes and volume (density) changes which may be represented by:

$$\Delta\left(\frac{u^2}{2}\right) + \Delta\left(\frac{P}{\rho}\right) = 0, \tag{3}$$

then, it follows that $$\frac{Q^2}{2A_2^2} - \frac{Q^2}{2A_1^2} = \frac{\Delta P}{\rho} + P\Delta\left(\frac{1}{\rho}\right), \tag{4}$$

or more simply, $$\frac{Q^2}{2}\left(\frac{1}{A_2^2} - \frac{1}{A_1^2}\right) = \frac{\Delta P}{\rho}\left(1 - \frac{aP}{aP+b}\right), \tag{5}$$

where Q is the flow rate, ΔP is the pressure differential between Venturi inlet portion 206 and Venturi throat portion 210, and $A_1$, $A_2$ are the cross sectional areas of Venturi inlet portion 206 and Venturi throat portion 210, respectively.

Review of above reveals that, with the exception of the terms in brackets on the right hand side, equation (5) is the typical Bernoulli equation relating differential pressure ΔP, mixture density and flow rate through a Venturi. Moreover, equation (5) could be modified to reflect slight losses in energy in the flow (i.e. take into account the change in density below the bubble point) by including a "discharge coefficient", $C_d$, as a differential pressure multiplier, wherein $C_d$, is a function of pressure P and the coefficients a and b. Adding this discharge coefficient, $C_d$, to equation (5) gives:

$$\frac{Q^2}{2}\left(\frac{1}{A_2^2} - \frac{1}{A_1^2}\right) = \frac{\Delta P}{\rho} C_d^2, \tag{6}$$

wherein the value of the discharge coefficient, $C_d$, may be given by:

$$\left(1 - \frac{aP}{aP+b}\right) = C_d^2. \tag{7}$$

It should be appreciated that $C_d$ is typically a constant that is approximately equal to 1.0.

Given the above, then according to equation (6) with a discharge coefficient $C_d$ approximately equal to 1.0 and a given flow rate Q, the value of a will be equal to zero (0) for pressures above the bubble point. Additionally, if the flow rate Q is kept constant, but the absolute pressure P is reduced to a point below the bubble point, the value of a will change abruptly, the discharge coefficient $C_d$ will decrease according equation (7) and the differential pressure ΔP will increase according to equation (6). Thus, it can be predicted that the response of the Venturi to the pressure falling below the bubble point will be a step change (i.e. discontinuity) in differential pressure ΔP. It should also be appreciated that, according to equation (6) having a constant discharge coefficient $C_d$, the flow rate Q would experience a step change (i.e. discontinuity or dp_jump) as the pressure drops below the bubble point. As such, the absolute pressure P in Venturi inlet portion 206 can be interpreted as an approximation of the bubble point and while equation (7) suggests that the discharge coefficient $C_d$ is pressure dependent, at the very high down-hole pressures and relatively small changes in pressure during operation of the well, for practical purposes the discharge coefficient $C_d$ can be approximated as being constant with pressure.

To aid in understanding, consider the relationship between the flow rate Q and absolute pressure P in Venturi inlet portion 206, where the flow rate Q is given by equation (6) and the discharge coefficient $C_d$ is equal to 0.98. At a shut-in, the flow rate Q is nearly equal to zero (0) and the absolute pressure P is relatively high. As the well choke is opened, the flow rate Q increases and the absolute pressure P decreases and the flow rate Q will experience a step change (discontinuity) and increase suddenly due to a step change (discontinuity) in the differential pressure ΔP. The discontinuity in the apparent flow rate Q, referred to as the Delta-P or the dp_jump as discussed hereinabove, may actually be problematic. This is because in current processing algorithms that calculate the flow rate Q using a constant discharge coefficient $C_d$ approximately equal to 1.0 regardless of pressure P, the flow rate Q will be in error if the absolute pressure P is below the bubble point. Thus, it is desirable to be able to reliably determine the true flow rate Q regardless of the absolute pressure P.

It should be appreciated that true flow rate Q in a Venturi may be determined by generating differential pressure data ΔP and fluid density data ρ in real time and in a continuous manner. The differential pressure data ΔP and density data ρ may then be used to determine the true flow rate Q using the following relationship:

$$Q = kC_d \sqrt{\frac{\Delta P}{\rho}} ; \quad (8)$$

wherein the constant of proportionality k is a function of the dimensions of the Venturi, $C_d$ is the discharge coefficient calibrated on the surface to be equal to 0.98. It should be appreciated that the calculation of equation (8) may be performed in a manner responsive to two conditions: 1) a start-up or a shut-in condition where absolute pressure P changes rapidly, and 2) a condition where the pressure changes slowly with time. Each of these conditions are discussed further below.

One term that should be defined before the above two conditions are addressed is the term "Flow Pressure Relationship" or FPR. This is because FPR is a curve that is used herein in terms of down-hole pressure and flow rate instead of its traditional meaning relating to the measurement of surface flow rate. Additionally, models to parameterize FPR are also presented herein as a method for obtaining a 'snapshot' of the FPR from shut-in and start-up conditions of well production.

The pressure P in Venturi inlet portion 206 and the down-hole flow rate Q computed using equation (8) may be used to determine the FPR, which may in turn be used to determine the production rate when a certain backpressure is exerted at the wellhead. Additionally, the slope of the FPR curve may be monitored and used to reflect a change in the reservoir and/or fluid properties over time.

Figure 6:
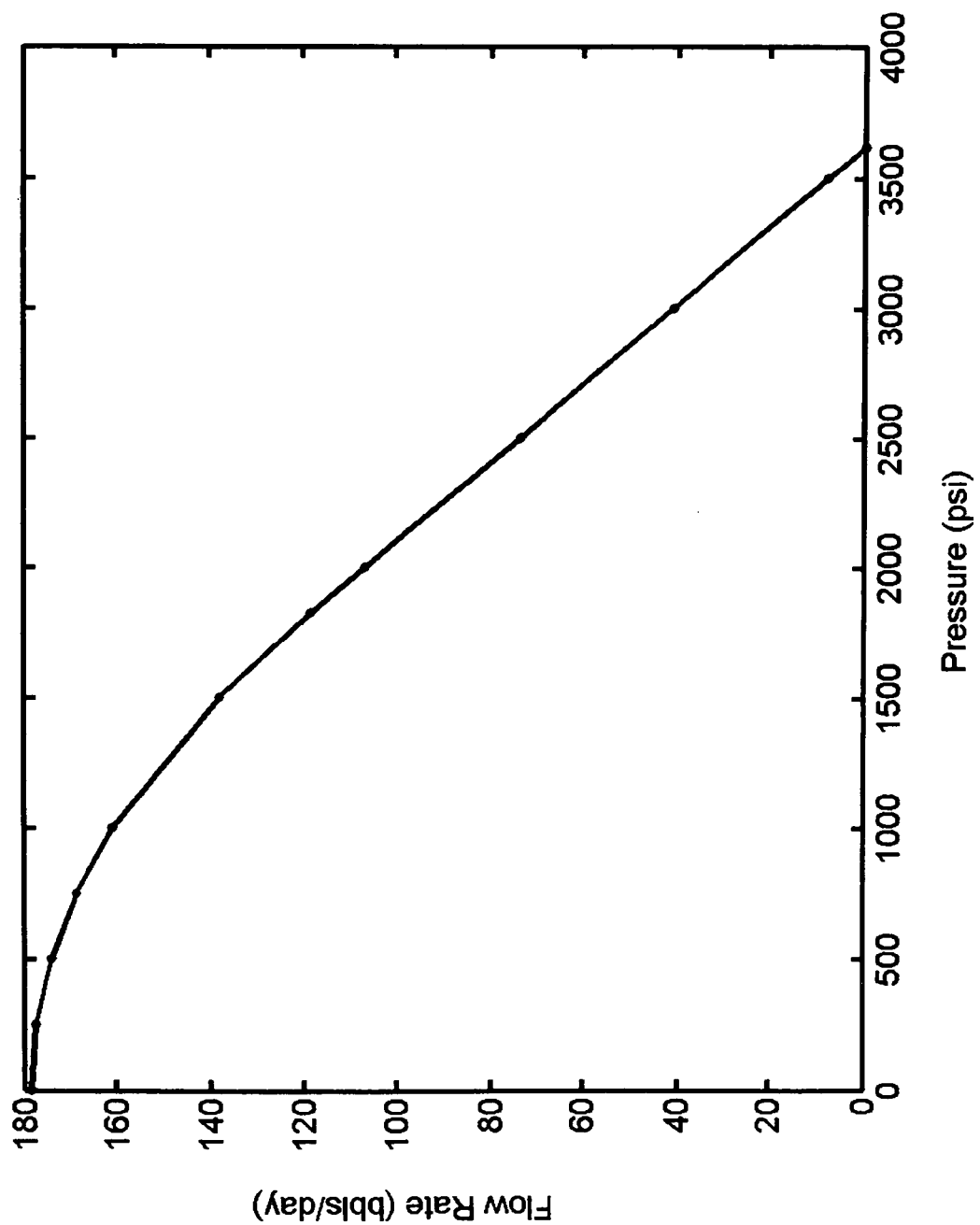
FIG. 6 is a graph illustrating the relationship between the flow rate and the pressure of a fluid in a saturated reservoir, in accordance with the prior art.

Referring to FIG. 6, surface flow rate versus pressure data from a saturated reservoir obtained from a multi-rate test is shown. The bubble point pressure is 1850 psia and was obtained from PVT analysis of the data. As can be seen from this curve, the relationship between pressure and flow rate is a smooth, continuous function and as is characteristic of saturated reservoirs, the slope decreases with decreasing pressure.

Furthermore, although an equation traditionally used to describe oil well performance in saturated oil wells is the Vogel equation:

$$\frac{Q}{Q_{\max}} = 1 - 0.2\left(\frac{P}{P_R}\right) - 0.8\left(\frac{P}{P_R}\right)^2, \quad (9)$$

for situations where the reservoir pressure is unknown and decreases with time as the reservoir is naturally depleted when fluid is produced, a relatively simple polynomial model may be considered, such as:

$$Q = k_2 P^2 + k_1 P + k_0; \quad (10)$$

where $k_0$, $k_1$ and $k_2$ are unknown parameters that can be determined from the pressure and flow rate data. However, it will be clear to those skilled in the art that other models could be used, as well.

As mentioned briefly above, traditionally the FPR is computed with the assumption that the flow rate Q has been measured when the reservoir is in a pseudo steady-state (PSS) condition, such as when the entire drainage volume of a well contributes to the production. Thus, a certain amount of time is usually required to reach the condition of PSS. However, in high permeability formations, where the permeability is in 10's of Darcies, the PSS condition is reached almost instantly.

Figure 7:
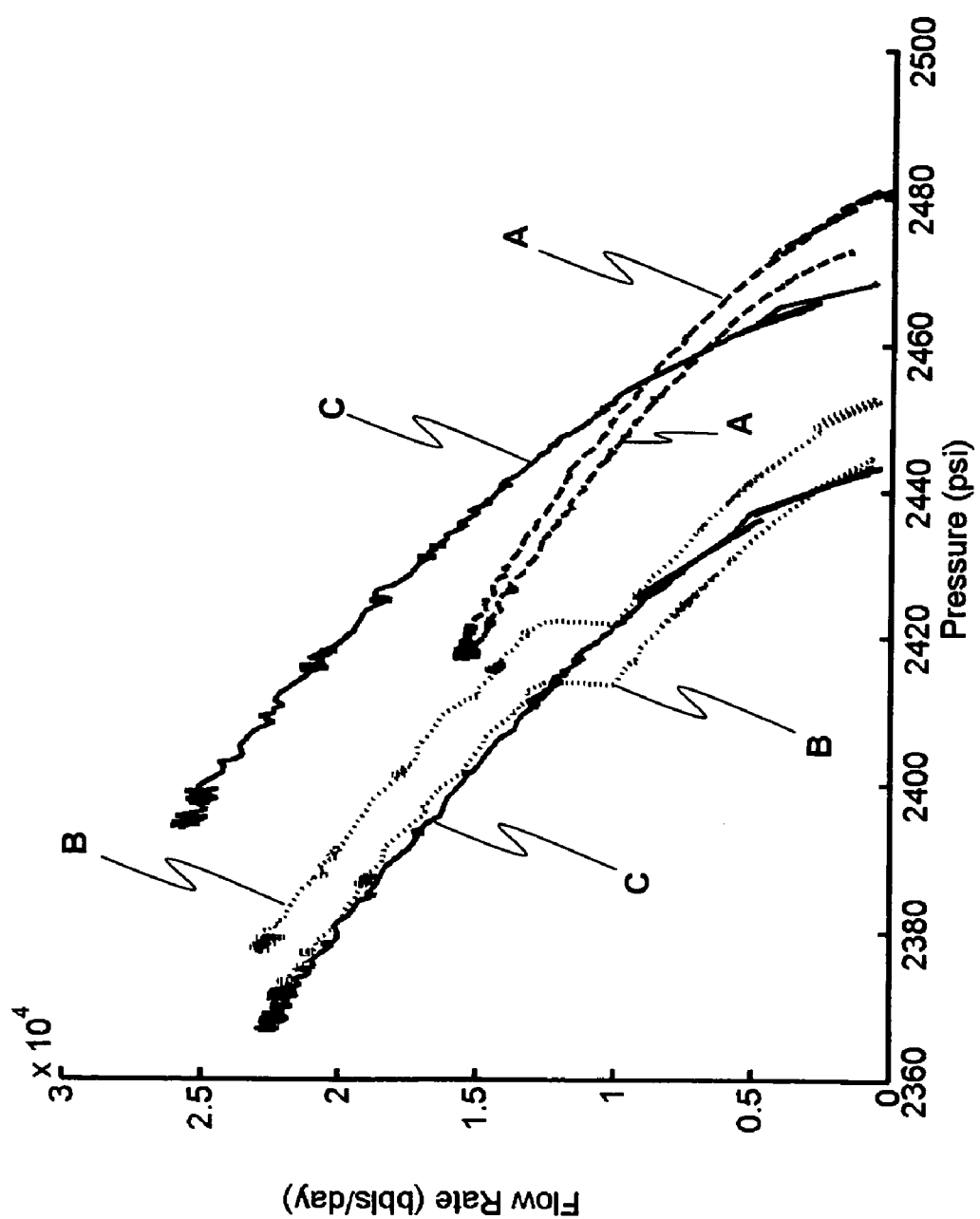
FIG. 7 is a graph illustrating the flow pressure relationship for three different modes in a well.

Consider an example where the well is shut-in often. These shut-in and start-up events offer a unique opportunity to map the complete FPR since the flow rate Q ranges from zero (0) to some maximum value that is dictated by the down-hole pressure and permeability of the formation. Referring to FIG. 7, the FPR curve comprises three different modes: the low pressure-drop mode (dashed trace A), the transition mode (dotted trace B) and the high pressure-drop mode (solid trace C).

The low pressure-drop mode (dashed trace A) is usually observed when the pressure in Venturi inlet portion 206 is above the bubble point pressure. The transition mode (dotted trace B) is characterized by a dp_jump at the transition pressure $P_{transition}$. In this case, apart from the FPR model parameters, the FPR curve is further parameterized by a modified discharge coefficient $C_{dm}$ and an unknown discharge coefficient $C_d$ (or equivalently by a scaling factor f) and the transition pressure $P_{transition}$ at which the dp_jump occurs. The discharge coefficient $C_d$ and therefore the flow rate $Q_{tp}$ below the transition pressure $P_{transition}$ are modified by a scaling factor f, which is typically between 0 and 1. For example, when the FPR is modeled by a quadratic polynomial, the FPR may be given by:

$$Q = k_2 P^2 + k_1 P + k_0 \quad \text{if } P \geq P_{transition} \quad (11)$$

$$Q_{tp} = \frac{1}{f}(k_2 P^2 + k_1 P + k_0) \quad \text{if } P < P_{transition}.$$

Once the scaling factor f is computed for the transition mode, the modified discharge coefficient $C_{dm}$ and flow rate $Q_{tp}$ below transition pressure $P_{transition}$ is given as:

$$C_{dm} = fC_d, \quad (12)$$

and, $$Q_{tp} = fQ, \quad (13)$$

respectively. The discharge coefficient $C_d$ and the flow rate Q above transition pressure $P_{transition}$ remain unaffected. The high pressure-drop mode (solid trace C) is often seen when the well has been producing below bubble point for a considerable time. Similar to the low pressure-drop mode (dashed trace A), the FPR curve for the high pressure-drop mode (solid trace C) is smooth and continuous but predicts an artificially high flow rate Q for a given fluid pressure relationship in comparison with the low pressure-drop mode (dashed trace A). All three modes can be determined by equations (9)–(10) or any other FPR model with the flow rate Q below the transition pressure $P_{transition}$ being scaled by a scaling factor f.

Figure 8:
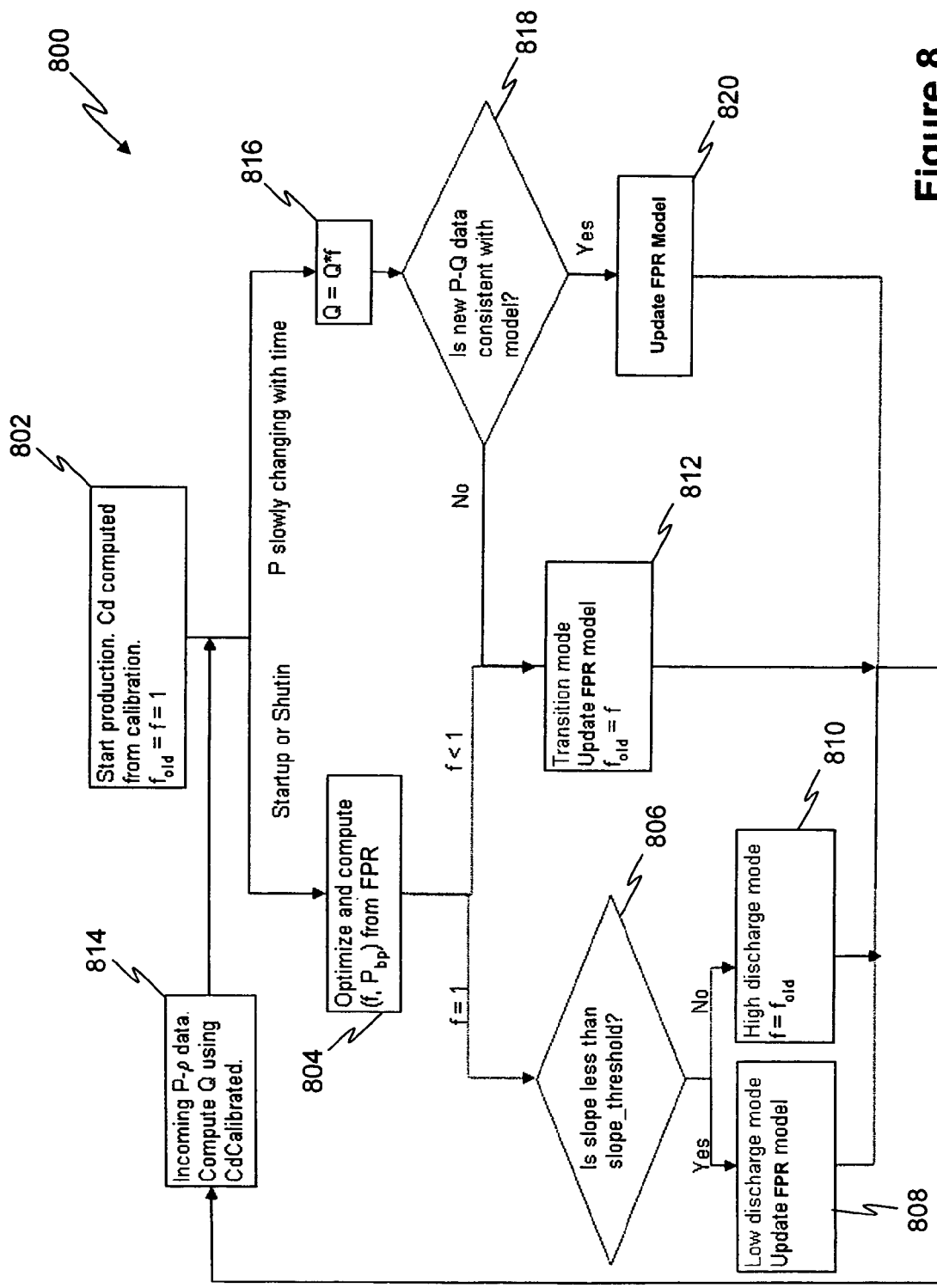
FIG. 8 is a block diagram illustrating a method for identifying the mode of operation in real-time, calculating the discharge coefficient for each mode and computing the corresponding modification of flow rate.

In light of the above, referring to FIG. 8, a method 800 for identifying the mode of operation in real-time, calculating an initial discharge coefficient $C_d$ (or equivalently by a scaling factor f) corresponding to each mode and computing the corresponding modification of flow rate Q is shown and includes determining the initial discharge coefficient $C_d$ from calibration upon production start-up, as shown in block 802. If production start-up has occurred, then optimize and calculate the bubble point pressure as a function of initial discharge coefficient $C_d$ (or scaling factor f) from the FPR, as shown in block 804. If the scaling factor f is equal to 1.0, then a determination is made as to whether the slope of the FPR is less than the slope_threshold, as shown in block 806. If the slope is less than the slope_threshold, then the FPR model is updated to reflect a "low discharge mode", as shown in block 808. However, if the slope is not less than the slope_threshold, then the FPR model is updated to reflect a "high discharge mode" and the calibrated discharge coefficient $C_{dm}$ is set to equal the initial discharge coefficient $C_d$, as shown in block 810. On the other hand, if the calibrated discharge coefficient $C_{dm}$ is less than 1.0, then the FPR is updated to reflect a transition mode (dotted trace B) and the calibrated discharge coefficient $C_{dm}$ is set to equal the initial discharge coefficient $C_d$, as shown in block 812. The incoming fluid pressure data, fluid density data and the calibrated discharge coefficient $C_{dm}$ are used to determine the flow rate Q and the data from at least one of block 808, block 810 and block 812 is communicated with the output of block 802, as shown in block 814.

However, if production start-up has not occurred and the pressure P is slowly changing with time, the flow rate Q is processed in a manner responsive to the initial discharge coefficient $C_d$ (or scaling factor f), as shown in block 816. A determination is then made as to whether the new pressure-flow rate data is consistent with the model, as shown in block 818. If the data is not consistent with the model, then the FPR is updated to reflect a transition mode (dotted trace B) and the calibrated discharge coefficient $C_{dm}$ is set to equal the initial discharge coefficient $C_d$, as shown in block 812. Conversely, if the data is consistent with the model, then the FPR model is updated to reflect this new data, as shown in block 820. The incoming fluid pressure data, fluid density data and the calibrated discharge coefficient $C_{dm}$ is used to determine the flow rate Q and the data from at least one of block 812 and block 820 is communicated with the output of block 802, as shown in block 814.

From the incoming pressure (both absolute pressure P and differential pressure ΔP) and density ρ data streams, the flow rate Q may be computed using equation (8) and the calibrated discharge coefficient, $C_{dm}$. As shown above, in the example of FIG. 10, the calibrated discharge coefficient $C_{dm}$ was calibrated on the surface to be 0.98 and the scaling factor f that relates the flow rate Q to the modified flow rate is initially set to 1.0.

It should be appreciated that when operated sufficiently slowly such that the well is in PSS, well start-ups and shut-ins may be used to provide the entire FPR curve. Although time periods wherein the pressure is changing very slowly with time provide additional information to the FPR curve, they are more complicated to analyze since the FPR may change with time as the reservoir depletes and the reservoir and fluid properties change with time. As such, time periods typically associated with rapid change in pressure, such as those that occur with well shut-ins and start-ups, are identified and processed separately from time periods corresponding to slow variation of pressure with time. In the field example above, well shut-ins are relatively rapid, where the flow rate goes to zero (0) in the order of a few minutes and the well may not be in PSS. Thus, in this example, data during shut-ins have not been considered for analysis. It should be appreciated that data obtained during well start-ups provide a map of the entire FPR profile with the well being in PSS as the flow rate increases.

It should also be appreciated that this may be accomplished using any approach and/or method suitable to the desired end purpose, such as a model-based approach and/or an observation based approach. In a model-based approach, the cavitation may be modeled based upon dynamics of fluid flow through a Venturi and is addressed simply in equations (1)–(7) hereinabove. In an observation-based approach, the underlying parameters may be obtained directly from obtained data. It should be appreciated that the analysis presented herein may be extended to a purely model-based approach, an observation-based approach and/or a mixture of the two approaches as well. Analysis of shut-ins and start-ups may be used to estimate the FPR model parameters, which in turn can be used to distinguish the low and high pressure-drop modes and identify dp_jumps in the subsequent steady-state data. Furthermore, if the mode of dissipation is well represented by the transition mode, two additional parameters, the scaling factor f and the transition pressure $P_{transition}$ may be estimated as well. The scaling factor f may then be used to compute a modified flow rate. Additionally, the scaling factor is related to the amount of gas released in the Venturi, which is in turn related to the PVT properties of the fluid.

It should be appreciated that shut-ins and start-ups may be analyzed by specifying an FPR model using equations (9)14 (10) or some other user-defined parameters. The modeled FPR may then be redefined by scaling the flow rate by a factor of 1/f below the bubble point pressure (as in equation (12)). A optimal estimate of the two model parameters f and $P_{transition}$ may then be determined by minimizing a cost function (such as the least squares function) of the FPR data with respect to the FPR model parameters. It should also be appreciated that this analysis is generalizable to other cost functions including a priori information incorporated through regularization functionals.

Figure 9:
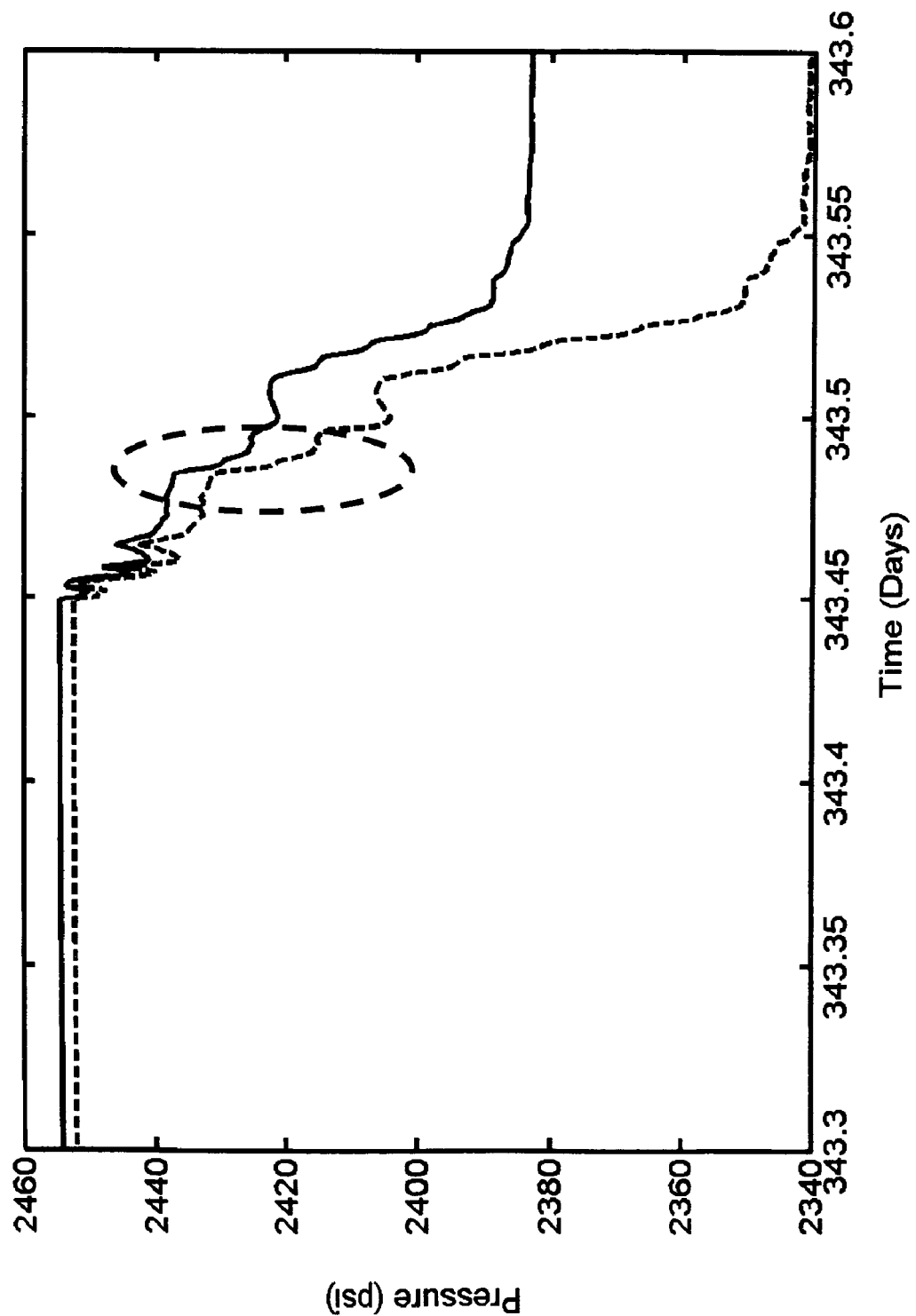
FIG. 9 is a graph of a well start-up over a time period of one day and illustrates the time period of the dp_jump for the flow meter of FIG. 2.
Figure 10:
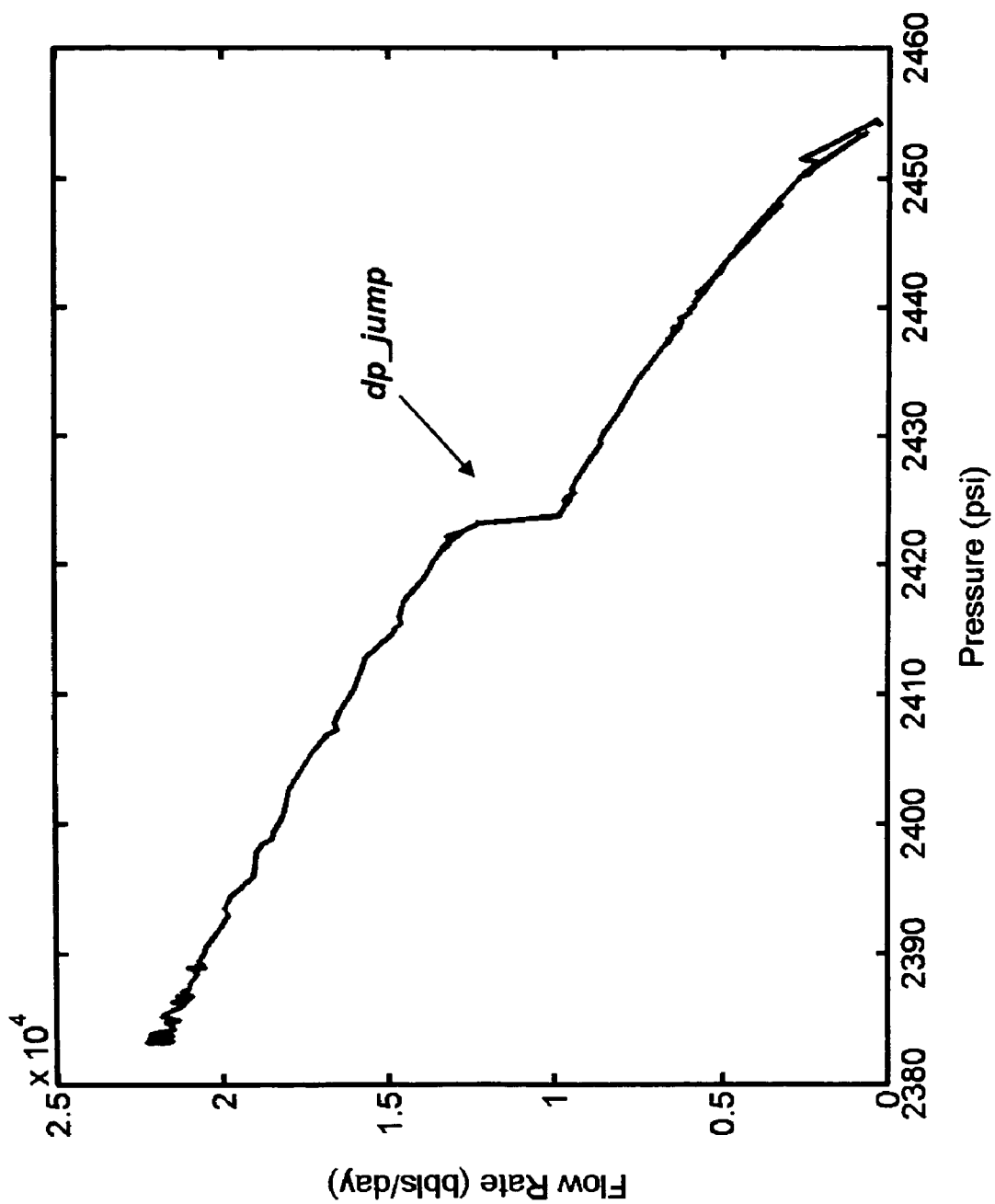
FIG. 10 is a graph illustrating the flow pressure relationship (FPR) for the time period of FIG. 9.
Figure 11:
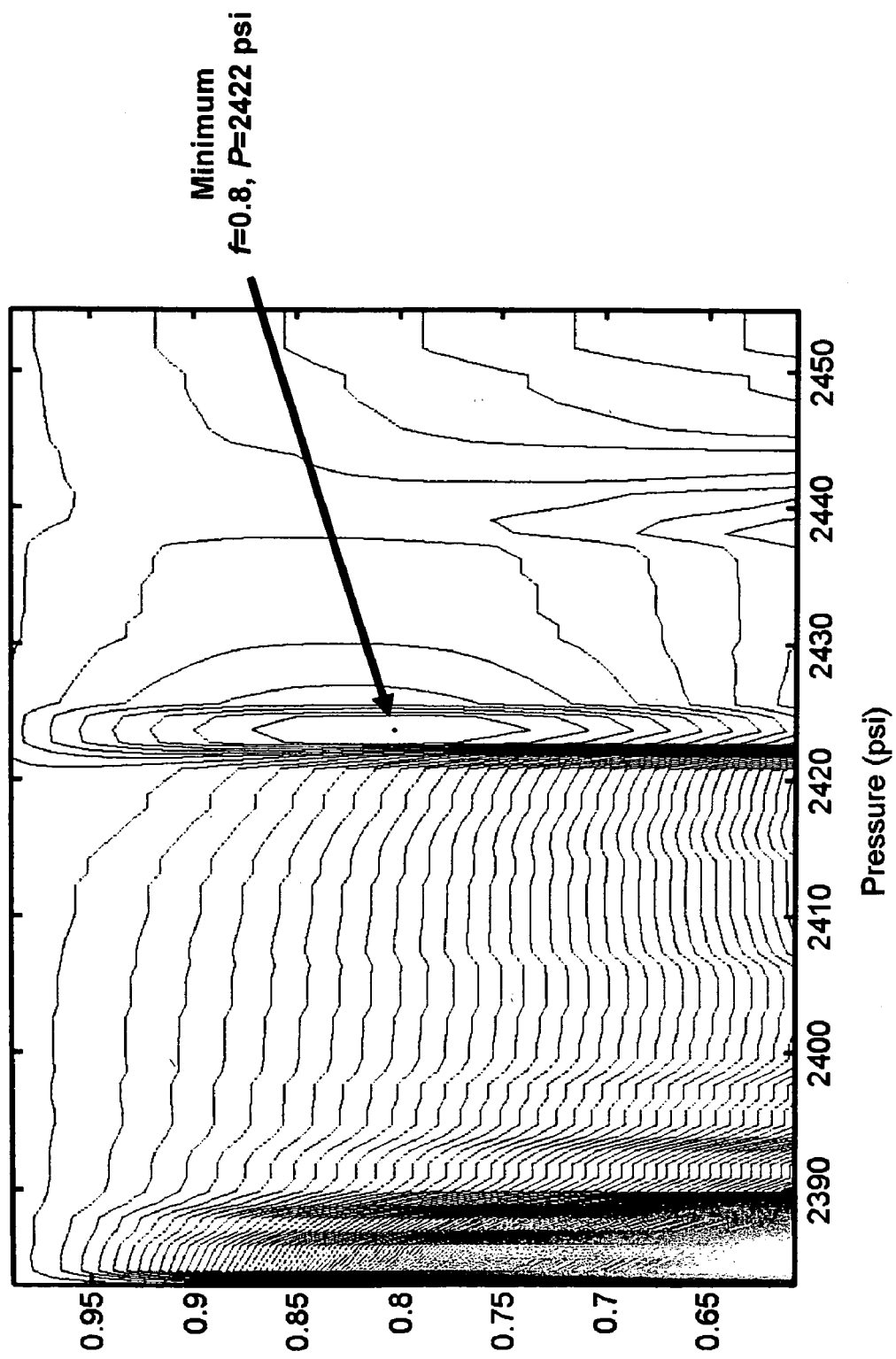
FIG. 11 is a contour plot of the least squares cost function for the graphs of FIG. 9 and FIG. 10.

Referring to FIG. 9, a graph illustrating a well start-up over the time period of one day for the field example is shown. The solid and dashed traces correspond to pressure at the Venturi inlet portion and the Venturi throat portion, respectively. The circled area shows the time period of the dp_jump. The corresponding FPR curve is shown in FIG. 10 and indicates the dp_jump (refer to the arrow in FIG. 10) in the flow rate at the bubble point pressure. Similarly, the contour plot of the least squares cost function from this data with a fit from equation (12) is as shown in FIG. 11. It should be apparent from the above that the cost function has only one minimum at f=0.8 and a $P_{transition}$=2422 psi. Thus, the optimal value of the two parameters can be used to modify the flow rate $Q_m$ as given by:

$$Q_m = fQ, P < P_{transition}$$

$$Q_m = Q, P \geq P_{transition} \quad (14)$$

Figure 12:
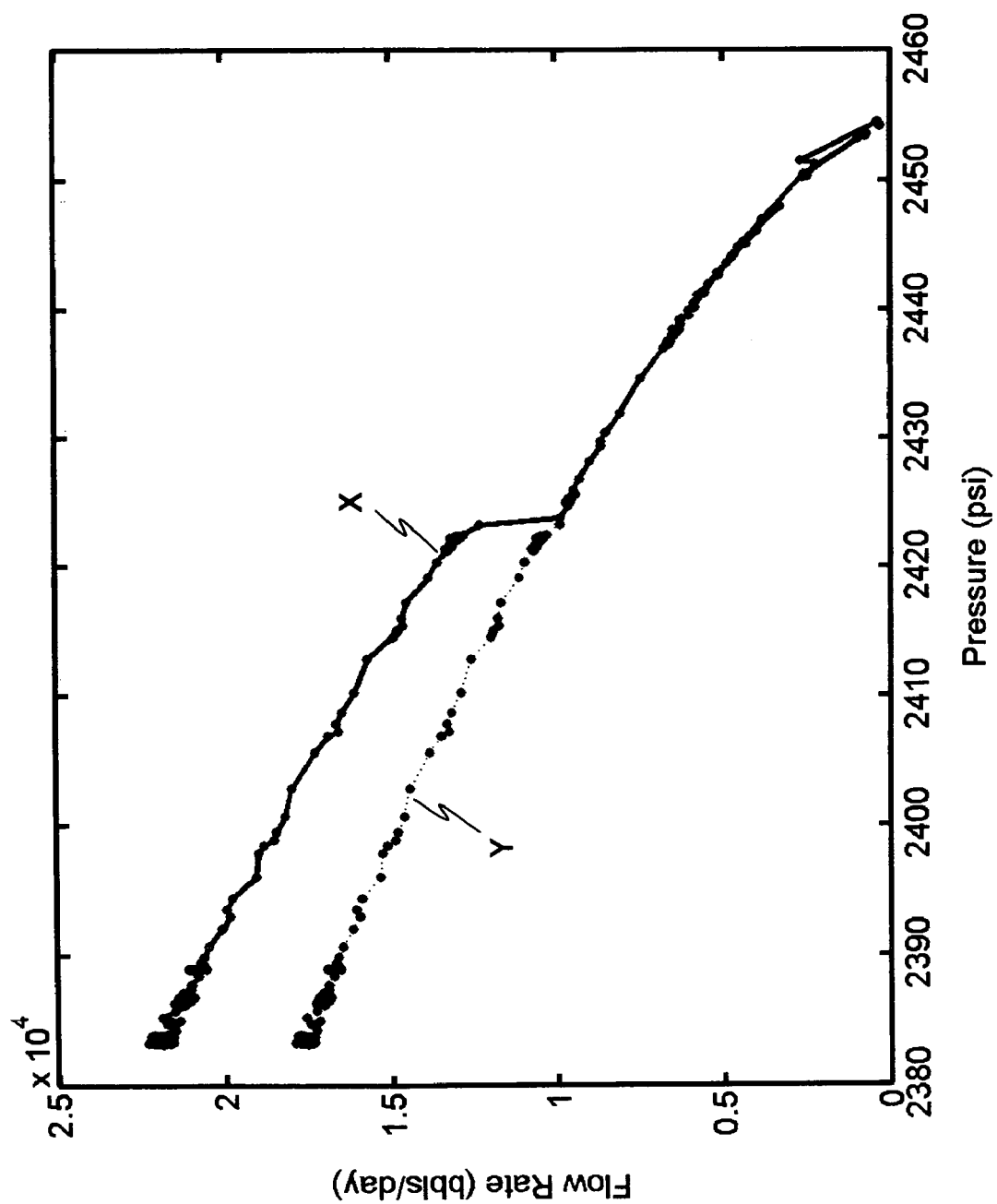
FIG. 12 is a graph showing the flow pressure relationship for a flow meter before and after the modification of flow rate.

FIG. 12 shows the FPR curve before X (solid trace) and after Y (dashed trace) the modification of flow rate Q to consider the dp_jump. It should be appreciated that although the transition mode can be distinguished from the high and low pressure drop modes, the latter two modes are indistinguishable from each other based on just scaling parameter since f=1. However, the first and second order derivatives are different for the FPR curve in the high and low pressure-drop modes and can be used to distinguish the two.

Figure 13:
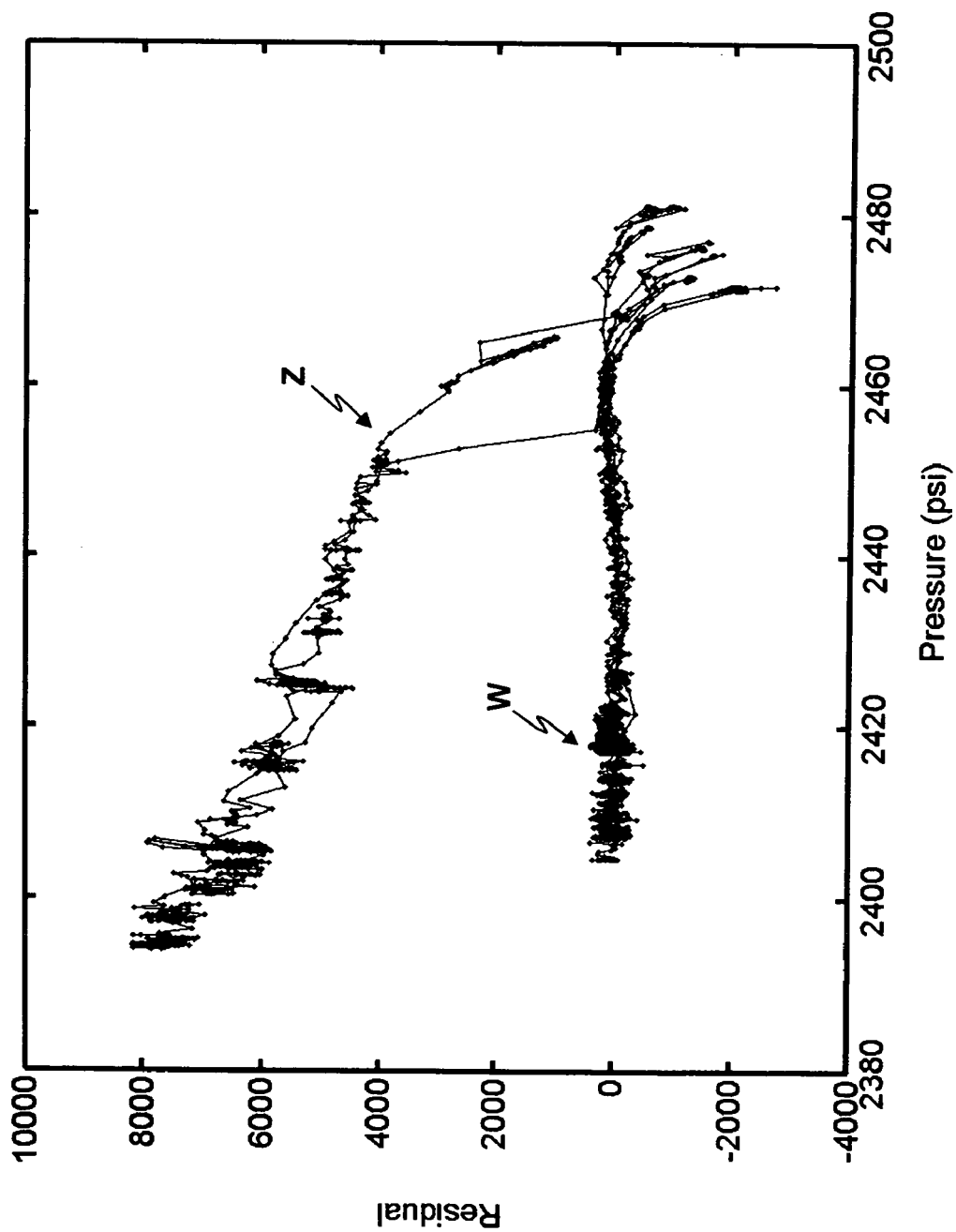
FIG. 13 is a graph illustrating the relationship between residual flow rate and pressure in a Venturi.
Figure 14A:
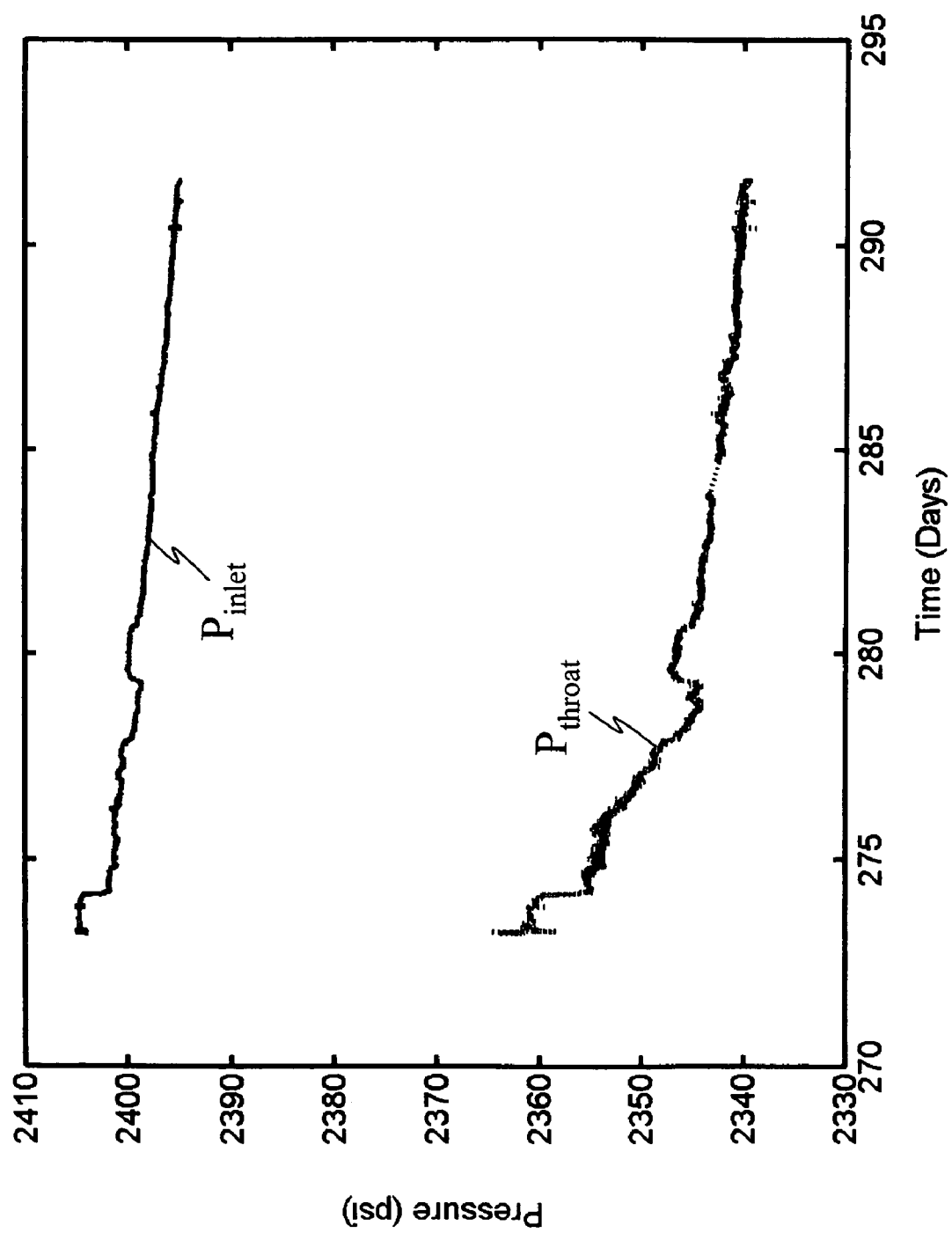
FIG. 14(a) is a graph showing the pressure in the inlet and throat of a Venturi.
Figure 14B:
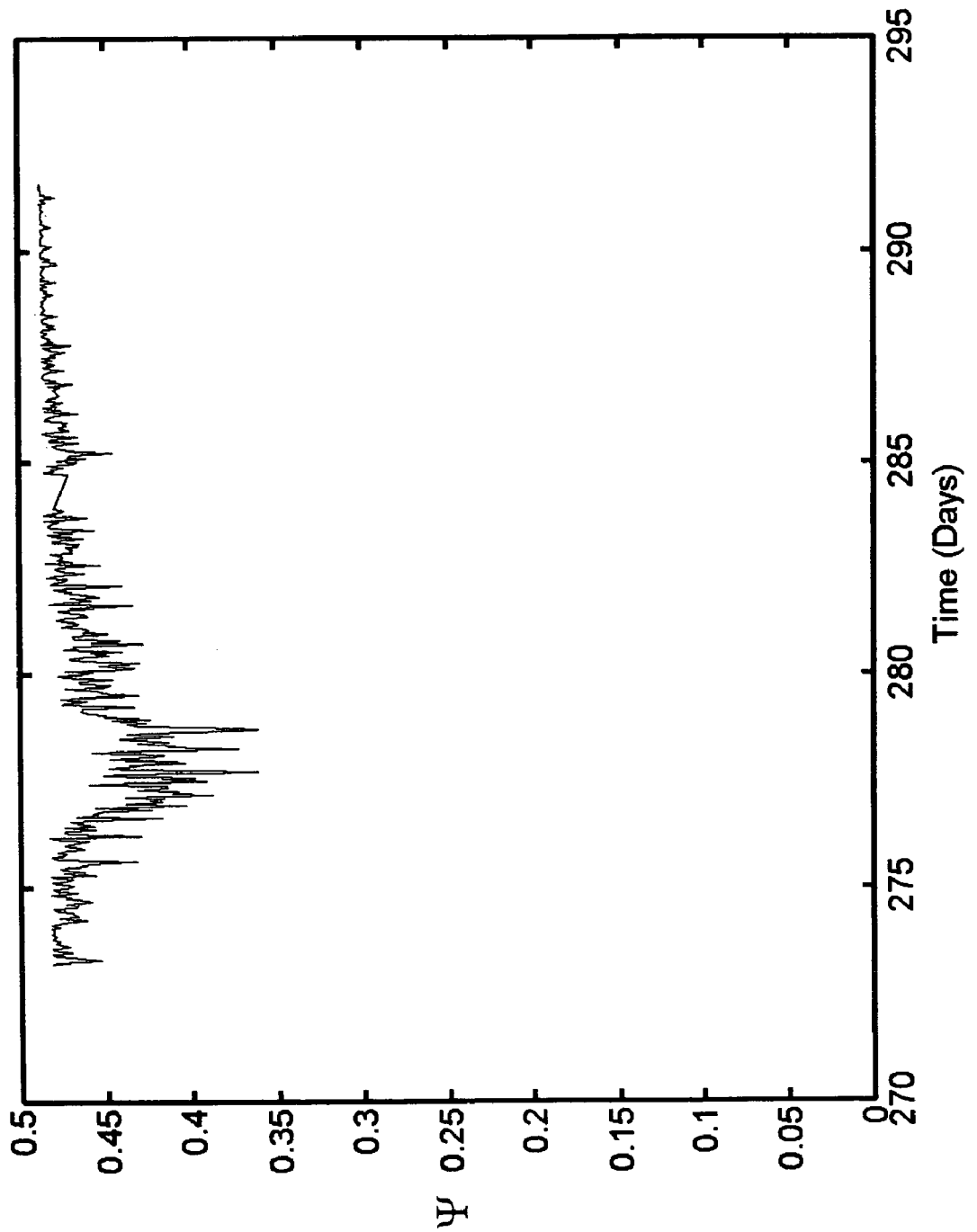
FIG. 14(b) is a graph of the probability of the data in FIG. 14(a) coming from an FPR model.
Figure 14C:
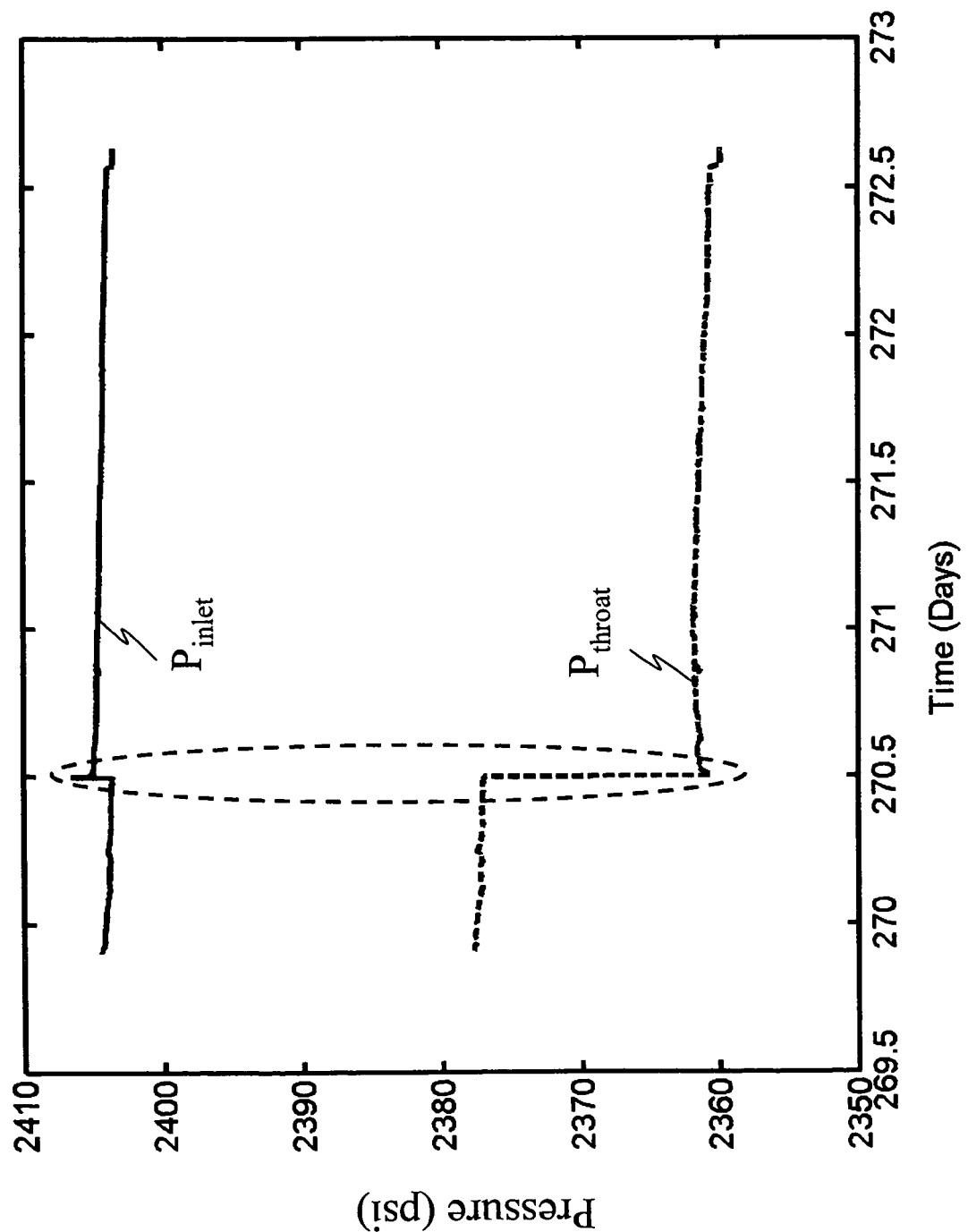
FIG. 14(c) is a graph showing the pressure in the inlet and throat of a Venturi showing a dp_jump.
Figure 14D:
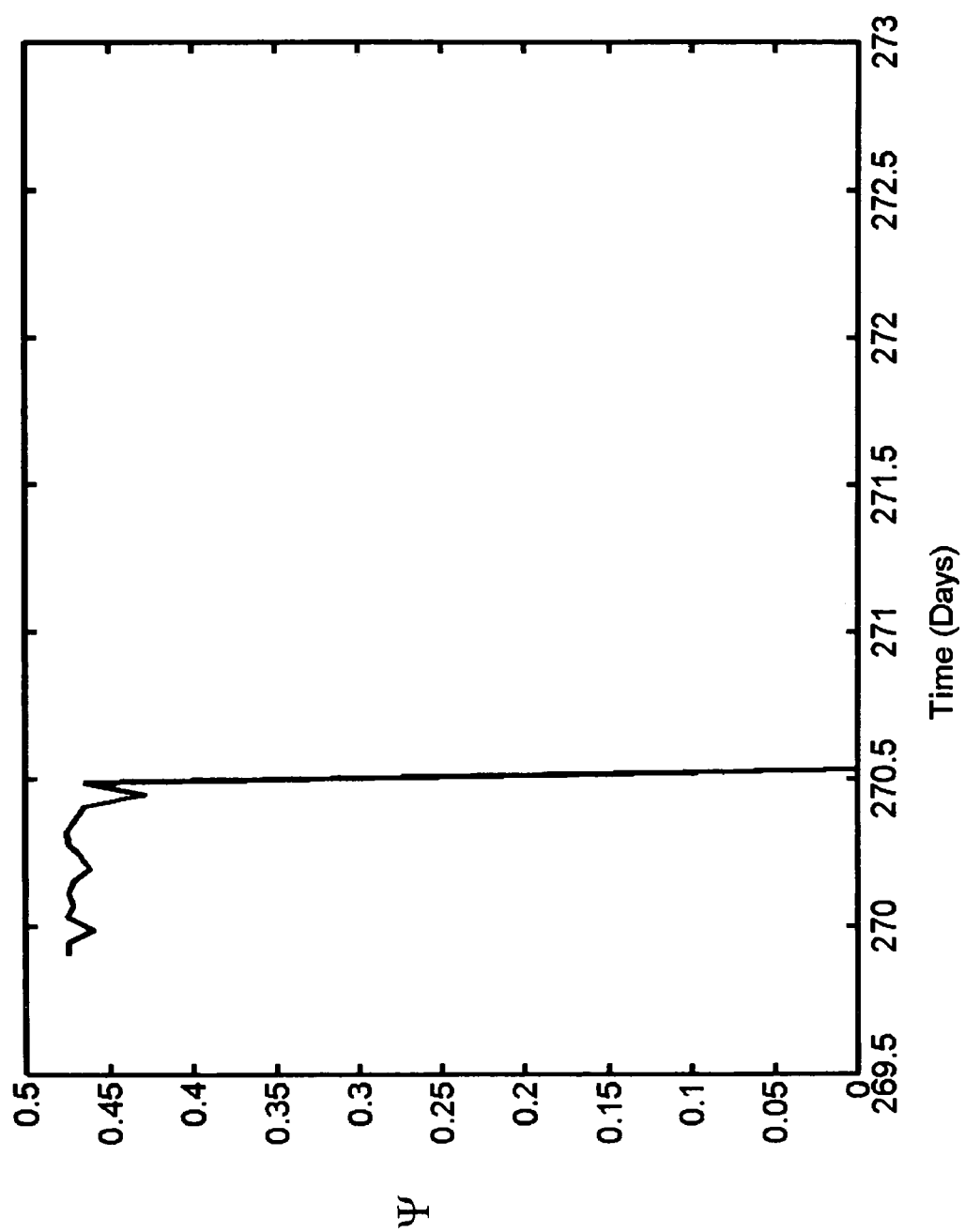
FIG. 14(d) is a graph of the probability of the data in FIG. 14(c) coming from an FPR model.

One method for distinguishing between the two modes includes assuming that the fluid at the location of the flow meter is above the bubble point at the start of production and assuming that the very first shut-in corresponds to the low pressure-drop mode. The estimate of the FPR model parameters thus may be taken as reference parameters and used to distinguish the two modes for subsequent shut-ins and start-ups. For any subsequent start-up after shut-in, an optimal estimate for the FPR model parameters may be computed. Next, a residual signal defined as the difference between the FPR and the fit from the reference parameters over the same range of inlet Venturi pressure may be computed. As can be seen from FIG. 13, the low pressure-drop modes W have an almost zero (0) slope while the high pressure-drop modes Z have an appreciable slope. Therefore, a slope threshold defined in this domain can be used to distinguish between the low and high pressure-drop modes.

Subsequent to the shut-in and start-up, as the pressure data are slowly varying with time, the pressure at the Venturi inlet portion may fall below the bubble point pressure giving rise to a dp_jump in the FPR data. In this scenario, the identification of the dp_jump is made more complicated since the reservoir properties and therefore the FPR curve are gradually changing with time. It should be appreciated that if a dp_jump is present, the dp_jump can be determined, along with the probability that the incoming real-time data are consistent with the latest FPR model in a plurality of ways. One such way, includes assuming that the data used is from the FPR model and the model parameters are updated using a recursive least-squares method. The flow rates between [−1 1] are then normalized and the FPR curve and subsequent recursive least squares using real-time data using Chebyshev polynomials are parameterized. Correspondingly, the matrix that is inverted is better conditioned as compared to the corresponding Vanderbilt matrix. The gradual change of the FPR curve profile with time due to change in reservoir properties is accommodated by introducing a weighting factor λ that can be used to provide a lower weight to data samples in the distant past. The chi-square value $\chi^2$ is computed and the goodness of fit of the data to the model is estimated. The probability $\Psi$ that a value of chi-square as poor as the value in equation (14) should occur by chance may then be computed using, $$\Psi = G\left(\frac{N-2}{2}, \frac{\chi^2}{2}\right), \quad (15)$$

where G is the incomplete Gamma function and N is the number of data points. If $\Psi$ is very small (example, $\Psi$<0.01), it is possible to conclude that the data are inconsistent with the model and may signal an event such as a dp_jump.

As can be seen by referring to FIGS. 14(*a*) and 14(*b*), the incomplete Gamma function, as a function of pressure, in the inlet and throat of the Venturi. In FIG. 14(*a*), the pressure data are slowly varying with time. However, since there are no events such as a dp_jump in the data, the corresponding probability in FIG. 14(*b*) $\Psi$ remains quite large and is between 0.3 and 0.5. Referring to FIG. 14(*c*), the dp_jump is circled and is evident at around day 270.5 and correspondingly, referring to FIG. 14(*d*), the function $\Psi$ suddenly transitions to zero (0) when an update of the FPR model with the data corresponding to the dp_jump is attempted, it is shown to be inconsistent with the FPR model.

Figure 15A:
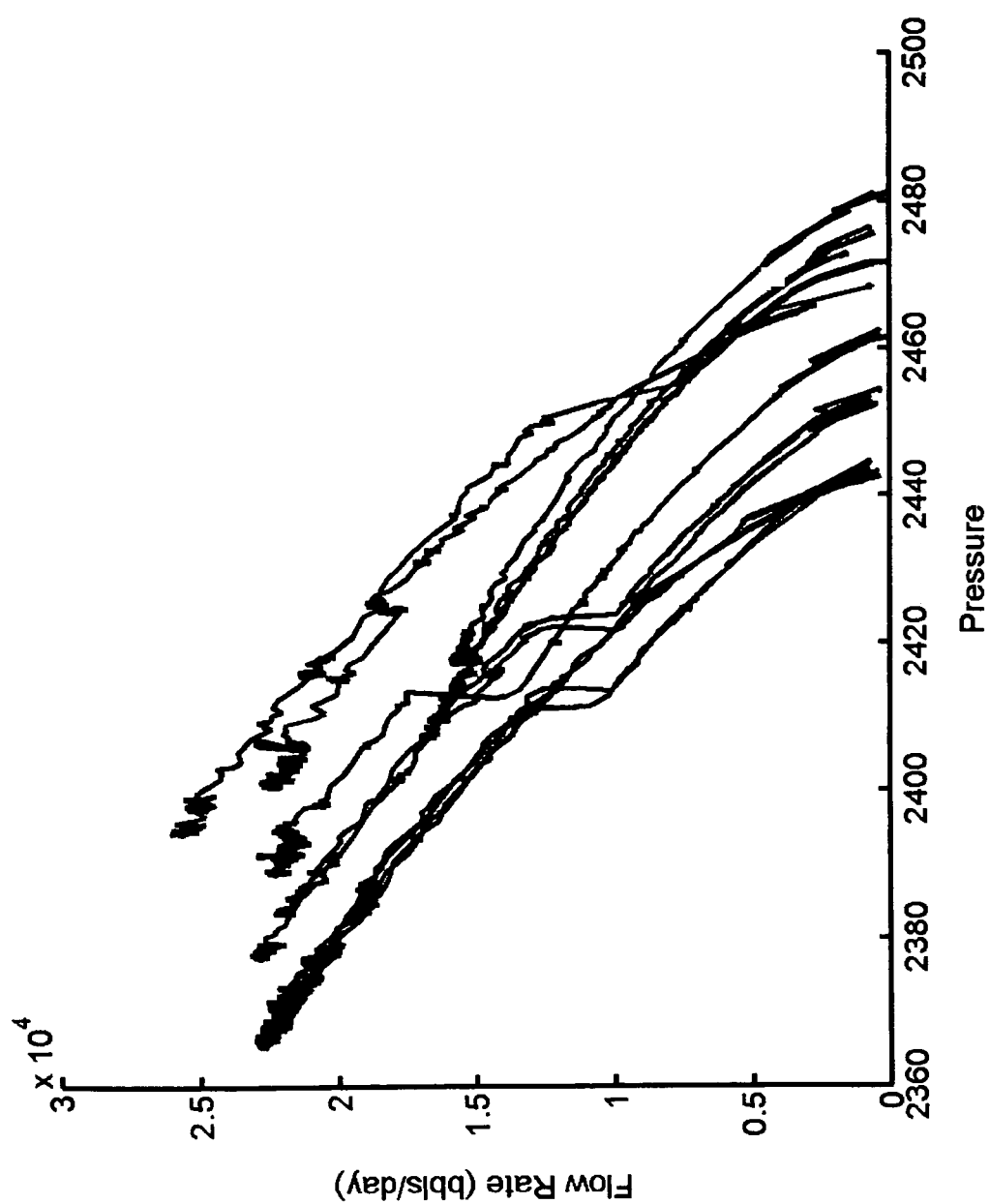
FIG. 15(a) is a graph showing the fluid pressure relationship of the apparent flow rate over a period of eight (8) months.

It should be appreciated that this analysis may also be used to monitor fluid pressure relationships. For example, referring to FIGS. 15(*a*) and 15(*b*), the fluid pressure relationships over the period of 8 months in the field example from various start-ups before and after the flow rate is corrected to account for the dp_jump are shown. The slope of the different FPR curves are different in FIG. 15(*a*) suggesting that the reservoir is changing with time. On the other hand, when the flow rate is corrected for the dp_jump, it is evident from FIG. 15(*b*) that the reservoir is not changing with time and since the curves are parallel to each other, accordingly there is no free gas in the formation.

It should be appreciated that although the analysis presented herein is done in the pressure-flow rate domain, any other domain defined by pressure and a dependence of differential pressure suitable to the desired end purpose may be used as well. Moreover, the analysis described herein is accomplished using recursive least-squares on a linear model between pressure and flow-rate. However, it should be appreciated that the analysis is generalizable on linear and non-linear models by use of Kalman filters and/or Bayesian analysis. Similarly, although the analysis presented above considers the scaling factor f to be a constant below the bubble point pressure, the analysis is readily generalizable to a gradual change in the scaling factor f with pressure below bubble point pressure.

Moreover, although the diagnostic signal as described herein to identify the onset of cavitation is the pressure difference between the Venturi inlet portion 206 and the Venturi throat portion 210, it should be appreciated that other signals may be used to identify the onset of cavitation. Any signal that responds differently to the higher volume of vapor just downstream of the cavitation device compared to the lower volume of vapor just upstream of the cavitation device can be used to identify the onset of cavitation. Such a signal would be expected to exhibit an abrupt change with the onset of cavitation. These signals include, but are not limited to, velocity of the fluid by various techniques, including cross correlation, miniature spinners, ultrasonic or laser doppler (velocity in the downstream, gassy region will be higher than in the upstream gas-free region); density of the fluid (density in the downstream, gassy region will be less than in the upstream gas-free region); dielectric constant, if the fluid is water free (average dielectric constant in the downstream, gassy region will be less than in the upstream gas-free region); water holdup by various techniques, including microwave, x-ray, and capacitance (if there is some water flowing in addition to hydrocarbons, the water holdup will be less in the downstream, gassy region than in the upstream gas-free region) and acoustic noise (the level of acoustic noise will be greater in the downstream, gassy region than in the upstream gas-free region).

Furthermore, although the step change in Venturi pressure difference is used to calibrate a different discharge coefficient above and below the bubble point, it should be appreciated that other signals could be used to calibrate a different discharge coefficient above and below the bubble point, for either a Venturi or orifice flow meter. Moreover, although the disclosed embodiments for generating locally lower pressure have been described in terms of a Venturi, it should be appreciated that other methods to generate locally lower pressure and therefore cavitation may be used. For example, a simple orifice may be used to create a pressure drop and therefore cavitation. Intense ultrasonic waves also produce locally produce locally lower pressure at the troughs of the acoustic wave and can produce cavitation. An impeller, driven or static, in the flow can also produce locally lower pressure. All of these devices have the effect of increasing the volume of vapor in the flow just downstream of the device compared to the flow just upstream of the device. It should also be appreciated that the term flowing well, is intended to include all flowing wells, including wells with cross flow, producing wells and wells where fluid flow to the surface.

As described above, one or all of the methods 100, 300 and 400 of FIGS. 1, 3 and 4, respectively, in whole or in part, may be embodied in the form of computer-implemented processes and apparatuses for practicing those processes. The methods 100, 300 and 400 of FIGS. 1, 3 and 4, respectively, in whole or in part, may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) may be updated to implement the methods 100, 300 and 400 of FIGS. 1, 3 and 4, respectively, in whole or in part.

Also as described above, the methods 100, 300 and 400 of FIGS. 1, 3 and 4, respectively, in whole or in part, may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments may configure the microprocessor to create specific logic circuits.

While the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A method for determining the true flow rate of a fluid in a flow line of a flowing well, comprising:
   modifying fluid pressure in a predetermined region of the flow line;
   generating pressure data responsive to the flow line;
   obtaining apparent flow rate data responsive to said pressure data;
   identifying a discontinuity in said apparent flow rate data, wherein said discontinuity is responsive to a release of gas from the fluid; and
   generating true flow rate data responsive to the relationship $$Q = kC_d \sqrt{\frac{\Delta P}{\rho}},$$

where Q is the true flow rate data, k is a function of the dimensions of a flowmeter, $C_d$ is a discharge coefficient, $\Delta P$ is pressure differential across said flowmeter and $\rho$ is fluid density.

2. The method of claim 1, wherein said modifying includes decreasing said fluid pressure in said predetermined region of the flow line using a Venturi.

3. The method of claim 1, wherein said pressure data includes at least one of an absolute pressure data and a differential pressure data.

4. The method of claim 1, wherein said apparent flow rate data includes at least one of density data, differential pressure data.

5. The method of claim 1, wherein said generating includes generating differential pressure data responsive to said predetermined region.

6. The method of claim 1, wherein generating includes generating differential pressure data responsive to a plurality of locations in the flow line.

7. The method of claim 6, wherein said plurality of locations in the flow line includes a first flow line location and a second flow line location.

8. The method of claim 1, wherein said identifying includes creating a graph responsive to said apparent flow rate data and visually examining said graph to identify said discontinuity.

9. The method of claim 1, wherein said identifying includes examining said apparent flow rate data using a processing device, and wherein said analyzing includes analyzing said discontinuity using said processing device.

10. The method of claim 1, wherein said generating includes determining a bubble point pressure responsive to said discontinuity.

11. The method of claim 1, wherein said identifying includes identifying said discontinuity by,
   obtaining a flow pressure relationship model and characteristic fluid data of the fluid
   determining a probability of consistency between said flow pressure relationship model and said characteristic fluid data, and processing said characteristic fluid data to create parameterized characteristic fluid data.

12. The method of claim 11, wherein said processing includes updating said flow pressure relationship model responsive to a mode of operation, wherein said mode of operation includes at least one of a low discharge mode, a transition mode and a high discharge mode.

13. The method of claim 11, wherein said processing further includes parameterizing said flow pressure relationship responsive to said characteristic fluid data to generate said parameterized characteristic fluid data.

14. The method of claim 11, wherein said processing further includes estimating a goodness of fit of said parameterized characteristic fluid data.

15. The method of claim 1, wherein said fluid density $\rho$ is represented by the relationship $\rho=aP+b$, where P is absolute pressure, a is the slope and b is an offset.

16. The method of claim 15, wherein said discharge coefficient, Cd, is a differential pressure multiplier responsive to said absolute pressure, P, said slope, a, and said offset, b.

17. The method of claim 15, wherein said discharge coefficient, Cd, is given by $$\left(1 - \frac{aP}{aP+b}\right) = C_d^2.$$

18. A method for determining the bubble point of a fluid in a flow line of a flowing well, comprising:
modifying fluid pressure in a predetermined region of the flow line;
generating pressure data responsive to the flow line, wherein said pressure data includes a differential pressure;
examining said pressure data to identify a discontinuity in said pressure data, wherein said discontinuity is caused by a release of gas from the fluid;
identifying said absolute pressure as the bubble point pressure; and generating absolute pressure data responsive to said discontinuity.

19. A method for identifying an occurrence of cavitation in a fluid flowing in a flow line, comprising:
generating at least one of fluid density data and true flow rate data responsive to the fluid, wherein said true flow rate data is generated via a method for determining a true flow rate comprising:
modifying a characteristic of the fluid,
generating fluid data responsive to said characteristic,
acquiring apparent flow rate data responsive to said fluid data,
examining said apparent flow rate data to identify indentifying a discontinuity in said apparent flow rate data, wherein said discontinuity is caused by at least one of cavitation and gas release from the fluid; and
generating said true flow rate data responsive to the relationship $$Q = kC_d\sqrt{\frac{\Delta P}{\rho}},$$

where Q is the true flow rate data, k is a function of the dimensions of a flowmeter, $C_d$ is a discharge coefficient, $\Delta P$ is pressure differential across said flowmeter and $\rho$ is fluid density;
communicating at least one of said true flow rate data and said fluid density data to a processing device; and
processing at least one of said true flow rate data and said fluid density data to determine whether cavitation has occurred, and generating cavitation data responsive to said processing.

20. A medium encoded with a machine-readable computer program code, the program code including instructions for causing a controller to implement a method for determining the true flow rate of a fluid in a flow line of a flowing well, the method comprising:
modifying fluid pressure in a predetermined region of the flow line;
generating pressure data responsive to the flow line;
obtaining apparent flow rate data responsive to said pressure data;
identifying a discontinuity in said apparent flow rate data, wherein said discontinuity is caused by at least one of cavitation and gas release from the fluid; and
generating true flow rate data responsive to the relationship $$Q = kC_d\sqrt{\frac{\Delta P}{\rho}},$$

where Q is the true flow rate data, k is a function of the dimensions of a flowmeter, $C_d$ is a discharge coefficient, $\Delta P$ is pressure differential across said flowmeter and $\rho$ is fluid density.

21. A method for determining the bubble point of a fluid in a flow line of a flowing well, comprising:
modifying fluid pressure in a predetermined region of the flow line;
generating pressure data responsive to the flow line;
examining said pressure data to identify a discontinuity in said pressure data, wherein said discontinuity is caused by a release of gas from the fluid;
identifying said absolute pressure as the bubble point pressure; and generating absolute pressure data responsive to said discontinuity.

22. The method of claim 21, wherein said modifying includes decreasing said local pressure using a Venturi.

23. The method of claim 21, wherein said identifying includes identifying a discontinuity by generating a graph of fluid flow rate versus said absolute pressure and identifying a step change on said graph.

24. A method for determining the true flow rate of a fluid in a flow line of a flowing well, comprising:
modifying fluid pressure in a predetermined region of the flow line;
generating pressure data responsive to the flow line;
obtaining apparent flow rate data responsive to said pressure data;
identifying a discontinuity in said apparent flow rate data, wherein said discontinuity is caused by a release of gas from the fluid; and
generating true flow rate data, wherein said true flow rate data is generated responsive to at least one of a discharge coefficient and a ratio between an absolute pressure and a pressure differential.

25. The method of claim 24, wherein said discharge coefficient is a function of said absolute pressure.

* * * * *